United States Patent
Chien et al.

(10) Patent No.: US 10,596,200 B2
(45) Date of Patent: Mar. 24, 2020

(54) USE OF LIFR OR FGFR3 AS A CELL SURFACE MARKER FOR ISOLATING HUMAN CARDIAC VENTRICULAR PROGENITOR CELLS

(71) Applicant: Procella Therapeutics AB, Tullinge (SE)

(72) Inventors: Kenneth R. Chien, Cambridge, MA (US); Xiaojun Lance Lian, University Park, PA (US)

(73) Assignee: Procella Therapeutics AB, Tullinge (SE)

( * ) Notice: Subject to any disclaimer, the term of this patent is extended or adjusted under 35 U.S.C. 154(b) by 963 days.

(21) Appl. No.: 14/984,783

(22) Filed: Dec. 30, 2015

(65) Prior Publication Data
US 2016/0108363 A1    Apr. 21, 2016

Related U.S. Application Data

(63) Continuation of application No. 14/832,324, filed on Aug. 21, 2015.

(60) Provisional application No. 62/194,016, filed on Jul. 17, 2015, provisional application No. 62/040,892, filed on Aug. 22, 2014.

(51) Int. Cl.
*A61K 35/34* (2015.01)
*G01N 33/50* (2006.01)

(52) U.S. Cl.
CPC ......... *A61K 35/34* (2013.01); *G01N 33/5014* (2013.01); *C12N 2501/235* (2013.01)

(58) Field of Classification Search
CPC ............. A61K 35/34; C12N 5/0657; C12N 2501/119; C12N 2501/235
See application file for complete search history.

(56) References Cited

U.S. PATENT DOCUMENTS

| 5,843,780 | A | 12/1998 | Thomson |
| 5,945,577 | A | 8/1999 | Stice et al. |
| 5,994,619 | A | 11/1999 | Stice et al. |
| 6,200,806 | B1 | 3/2001 | Thomson |
| 6,235,970 | B1 | 5/2001 | Stice et al. |
| 9,717,762 | B2 | 8/2017 | Wiencierz et al. |
| 2004/0180043 | A1 | 9/2004 | Sabbah et al. |
| 2005/0214260 | A1 | 9/2005 | Franco |
| 2006/0246446 | A1 | 11/2006 | Evans et al. |
| 2008/0038229 | A1 | 2/2008 | Minguell et al. |
| 2008/0182328 | A1 | 7/2008 | Snyder et al. |
| 2009/0162329 | A1 | 6/2009 | Anversa et al. |
| 2010/0093089 | A1 | 4/2010 | Marban |
| 2010/0166714 | A1 | 7/2010 | Chien et al. |
| 2011/0033430 | A1 | 2/2011 | Chien et al. |
| 2012/0009158 | A1 | 1/2012 | Chien et al. |
| 2012/0027807 | A1 | 2/2012 | Chien et al. |
| 2012/0301445 | A1 | 11/2012 | Blanpain et al. |
| 2013/0189785 | A1 | 7/2013 | Palecek et al. |
| 2013/0309769 | A1 | 11/2013 | Benvenisty et al. |
| 2014/0134733 | A1 | 5/2014 | Wu et al. |
| 2015/0252117 | A1 | 9/2015 | Chinn et al. |
| 2015/0297794 | A1 | 10/2015 | Yamashita et al. |
| 2016/0053229 | A1 | 2/2016 | Chien et al. |
| 2017/0067023 | A1 | 3/2017 | Yamashita et al. |
| 2017/0240964 | A1 | 8/2017 | Leung et al. |
| 2018/0148691 | A1 | 5/2018 | Chien et al. |
| 2019/0062696 | A1 | 2/2019 | Chien et al. |

FOREIGN PATENT DOCUMENTS

| WO | 9717762 A1 | 5/1997 |
| WO | 2009/017460 A1 | 2/2009 |
| WO | 2013/056072 A1 | 4/2013 |
| WO | 2014/150602 A1 | 9/2014 |

(Continued)

OTHER PUBLICATIONS

Wojakowski et al. "The role of CXCR4/SDF-1, CD117/SCF, and c-met/HGF chemokine signalling in the mobilization of progenitor cells and the parameters of the left ventricular function, remodelling, and myocardial perfusion following acute myocardial infarction" European Heart Journal Supplements (2008) 10 (Supplemen.*
Lauss et al. "Single inner cell masses yield embryonic stem cell lines differing in lifr expression and their developmental potential" Biochemical and Biophysical Research Communications 331 (2005) 1577-1586.*
U.S. Appl. No. 15/805,463, filed Nov. 7, 2017, Kenneth R. Chien.
U.S. Appl. No. 14/832,324, Feb. 15, 2018.
U.S. Appl. No. 15/805,463, Feb. 9, 2018.
Lian, X.J., et al.,"Robust cardiomyocyte differentiation from human pluripotent stem cells via temporal modulation of canonical Wnt signaling," PNAS,U. S. A., vol. 109(27), pp. E1848-E1857. (2012).
Lin, B. et al., High-purity enrichment of functional cardiovascular cells from human iPS cells, Cardiovascular Research, vol. 95(3), pp. 327-335 (Aug. 8, 2012).

(Continued)

*Primary Examiner* — Louise W Humphrey
*Assistant Examiner* — Stephen A Perkins
(74) *Attorney, Agent, or Firm* — Nelson Mullins Riley & Scarborough LLP; Jane E. Remillard, Esq.

(57) ABSTRACT

The present invention provides LIFR and FGFR3 as cell surface markers for isolating human cardiomyogenic ventricular progenitor cells, in particular progenitor cells that preferentially differentiate into cardiac ventricular muscle cells. Thus, the invention provides human ventricular progenitor (HVP) cells. The invention provides in vitro methods of the separation of Islet 1+ LIFR+ ventricular progenitor cells and/or Islet 1+/FGFR3+ ventricular progenitor cells and/or Islet 1+/LIFR+/FGFR3+ ventricular progenitor cells, and the large scale expansion and propagation thereof. Large clonal populations of isolated LIFR+ and/or FGFR3+ ventricular progenitor cells are also provided. Methods of in vivo use of LIFR+ and/or FGFR3+ ventricular progenitor cells for cardiac repair or to improve cardiac function are also provided. Methods of using the LIFR+ and/or FGFR3+ ventricular progenitor cells for cardiac toxicity screening of test compounds are also provided.

12 Claims, 11 Drawing Sheets

(56) References Cited

FOREIGN PATENT DOCUMENTS

| WO | 2015/058117 A1 | 4/2015 |
| --- | --- | --- |
| WO | 2016/029122 A1 | 2/2016 |
| WO | 2016/131137 A1 | 8/2016 |
| WO | 2017/172086 A1 | 10/2017 |
| WO | 2018/100433 A1 | 6/2018 |

OTHER PUBLICATIONS

Lin, Z. et al., "Strategies for cardiac regeneration and repair," Sci. Transl. Med., vol. 6, (239) 23 pages (2014).
Lui, K.O., et al., "Driving vascular endothelial cell fate of human multipotent Isl1+ heart progenitors with Vegf modified mRNA,". Cell Res., vol. 23, pp. 1172-1186. (2013).
Marks, A.R., "Calcium cycling proteins and heart failure: mechanisms and therapeutics," J. Clin. Invest, vol. 123, pp. 46-52. (2013).
Martin, U., "New muscle for old hearts: engineering tissue from pluripotent stem cells," Hum. Gene Ther., vol. 26, pp. 305-311. (2015).
Masters, M., et al., "The epicardium signals the way towards heart regeneration," Stem Cell Res., vol. 13, 683-692 (2014).
Masuda, S. et al., "Three-dimensional cardiac tissue fabrication based on cell sheet technology," Adv. Drug Deliv. Rev., vol. 96, pp. 103-109 (2016).
Masumoto, H., et al., "Human iPS cell-engineered cardiac tissue sheets with cardiomyocytes and vascular cells for cardiac regeneration," Sci. Rep., vol. 4 (6716) pp. 1-7 (2014).
Menasche', P. et al., "Human embryonic stem cell-derived cardiac progenitors for severe heart failure treatment: first clinical case report," European Heart Journal, vol. 36, pp. 2011-2017 (2015).
Min, J.Y. et al. "Significant improvement of heart function by cotransplantation of human mesenchymal stem cells and fetal cardiomyocytes in postinfarcted pigs," Ann. Thorac. Surg., vol. 74 (5),pp. 1568-1575 (2002).
Moretti, A., et al., "Multipotent embryonic isl1+ progenitor cells lead to cardiac, smooth muscle, and endothelial cell diversification," Cell, vol. 127(6), pp. 1151-1165 (2006).
Musunuru, K. et al., "Stem Cell Models of Cardiac Development and Disease," Annu Rev Cell Dev Biol., vol. 26, p. 667-687 (2010 ).
Niu, Y., et al.,"Generation of gene-modified cynomolgus monkey via Cas9/RNA-mediated gene targeting in one-cell embryos,". Cell, vol. 156, pp. 836-843. (2014).
O'Brien, T.X., et al., "Positional specification of ventricular myosin light chain 2 expression in the primitive murine heart tube," PNAS, U. S. A., vol. 90, pp. 5157-5161 (1993).
Oda, T. et al. "Mutations in the human Jagged1 gene are responsible for Alagille syndrome," Nat. Genet., vol. 16, p. 235-242 (1997).
Oda, T. et al. Identification and cloning of the human homolog (JAG1) of the rat Jagged1 gene from the Alagille syndrome critical region at 20p12, Genomics, vol. 43(3) pp. 376-379,(1997).
Orlic, D.et al., "Bone marrow cells regenerate infarcted myocardium" Nature, vol. 410, pp. 701-705 (2001).
Ott, H.C., et al., "Perfusion-decellularized matrix: using nature's platform to engineer a bioartificial heart.," Nat. Med., vol. 14, pp. 213-221, (2008).
Pagliuca, F.W., et al., "Generation of Functional Human Pancreatic beta Cells In Vitro," Cell, vol. 159(2), pp. 428-439 (2014).
Patel, A.K., et al., "A defined synthetic substrate for serum free culture of human stem cell derived cardiomyocytes with improved functional maturity identified using combinatorial materials microarrays," Biomaterials, vol. 61, pp. 257-265 (2015).
Perin, E.C. et al., "Transendocardial, autologous bone marrow cell transplantation for severe, chronic ischemic heart failure," Circulation, vol. 107, pp. 2294-2302 (2003).
Pittenger, M.F. , et al., "Mesenchymal Stem Cells and Their Potetial as Cardiac Therapeutics," Circ. Res. vol. 95, pp. 9-20 (2004).
Qyang, Y., et al. "The renewal and differentiation of Isl1+ cardiovascular progenitors are controlled by a Wnt/beta-catenin pathway," Cell Stem Cell, vol. 1, pp. 165-179. (2007).
Robitaille, J. et al."Mutant frizzled-4 disrupts retinal angiogenesis in familial exudative vitreoretinopathy," Nat. Genet., vol. 32, pp. 326-330 (2002).
Ruan, J.-L., et al., "Mechanical Stress Promotes Maturation of Human Myocardium from Pluripotent Stem Cell-Derived Progenitors," Stem Cells, vol. 33(7), pp. 2148-2157, (2015).
Rubin, L.L., "Stem cells and drug discovery: the beginning of a new era?" Cell, vol. 132(4), pp. 549-552. (2008).
Ruvinov, E., et al., "Alginate biomaterial for the treatment of myocardial infarction: Progress, translational strategies, and clinical outlook: From ocean algae to patient bedside," Adv. Drug Deily. Rev., vol. 96, pp. 54-76 (2016).
Sahara, M., et al.,"Programming and reprogramming a human heart cell," EMBO J., vol. 34(6), pp. 710-738 (2015).
Schaaf, S., et al., "Human engineered heart tissue as a versatile tool in basic research and preclinical toxicology," PLoS One, vol. 6(10), e26397, pp. 1-11 (2011).
Schwan, J., et al., "Prospects for In Vitro Myofilament Maturation in Stem Cell-Derived Cardiac Myocytes," Biomarker Insights, vol. 10, pp. 91-103 (2015).
Segers, V.F.M.,et al., "Stem-cell therapy for cardiac disease," Nature, vol. 451, pp. 937-942 (2008).
Senyo, S.E., et al., "Mammalian heart renewal by pre-existing cardiomyocytes," Nature, vol. 493(7432), pp. 433-436. (2013).
Shultz, L.D., et al., "Human lymphoid and myeloid cell development in NOD/LtSz-scid IL2R gamma null mice engrafted with mobilized human hemopoietic stem cells," J. Immunol., vol. 174, pp. 6477-6489 (2005).
Später, D., et al., "How to make a cardiomyocyte," Development, vol. 141(23), pp. 4418-4431 (2014).
Später, D., et al.,"A HCN4+ cardiomyogenic progenitor derived from the first heart field and human pluripotent stem cells," Nat. Cell Biol., vol. 15, pp. 1098-1106 (2013).
Stamm, C. et al."Autologous bone-marrow stem-cell transplantation for myocardial regeneration," Lancet, vol. 361, pp. 45-46 (2003).
Tanaka, S. et al., "A novel frizzled gene identified in human esophageal carcinoma mediates APC/beta-catenin signals," PNAS USA, vol. 95, pp. 10164-10169 (1998).
Thomson, J.A. et al., "Embryonic stem cell lines derived from human blastocysts," Science, vol. 282, pp. 1145-1147 (1998).
Tulloch, N.L., et al., "Growth of engineered human myocardium with mechanical loading and vascular co-culture," Circ. Res., vol. 109(1), pp. 47-59.(2011).
Van Laake, L.W., et al., "Human embryonic stem cell-derived cardiomyocytes survive and mature in the mouse heart and transiently improve function after myocardial infarction," Stem Cell Res., vol. 1, pp. 9-24. (2007).
Vanhoof, D. et al., "Identification of Cell Surface Proteins for Antibody-Based Selection of Human Embryonic Stem Cell-Derived Cardiomyocytes," Journal of Proteome Research, vol. 9(3), pp. 1610-1618 (Mar. 2010).
Vunjak-Novakovic, G., et al.,"Bioengineering heart muscle: a paradigm for regenerative medicine," Annu. Rev. Biomed. Eng., vol. 13, pp. 245-267. (2011).
Wang, G.,et al., "Modeling the mitochondrial cardiomyopathy of Barth syndrome with iPSC and heart-on-chip technologies," Nat. Med., vol. 20(6), pp. 616-623 (2014).
Wang, J., et al., "Cardiomyopathy associated with microcirculation dysfunction in laminin alpha4 chain-deficient mice," J. Biol. Chem., vol. 281, pp. 213-220 (2006).
Webber, M.J., et al., "A Perspective on the Clinical Translation of Scaffolds for Tissue Engineering," Ann. Biomed. Eng., vol. 43, pp. 641-656. (2014).
Yang, L., et al., "Human cardiovascular progenitor cells develop from a KDR+ embryonic-stem-cell-derived population," Nature 453, 524-528. (2008).
Yang, Z., "Cardiac overexpression of A1-adenosine receptor protects intact mice against myocardial infarction," Am J Physiol Heart Circ Physiol , vol. 282, pp. H949-H955 (2002).

(56) References Cited

OTHER PUBLICATIONS

Ye, L., et al., "Fabrication of a myocardial patch with cells differentiated from human-induced pluripotent stem cells," Methods Mol. Biol., vol. 1299, pp. 103-114.(2015).
Yi, A. et al., "Pregenerative medicine: developmental paradigms in the biology of cardiovascular regeneration," The Journal of Clinical Investigation, vol. 120(1) pp. 20-28 (2010).
Van Berlo, J. et al., "An emerging consensus on cardiac regeneration," Nat. Med., vol. 20(12): 1386-1393 (2014).
Yu, J. et al., "Human induced pluripotent stem cells free of vector and transgene sequences," Science, vol. 324(5928), pp. 797-801 (2009).
Zangi, L., et al., "Modified mRNA directs the fate of heart progenitor cells and induces vascular regeneration after myocardial infarction," Nat. Biotechnol., vol. 31(10), pp. 898-907 (2013).
Zhang, J. et. al., "Extracellular matrix promotes highly efficient cardiac differentiation of human pluripotent stem cells: The matrix sandwich method," Circ. Res., vol. 111, pp. 1125-1136 (2012).
Zhou, B., et al., "Epicardial progenitors contribute to the cardiomyocyte lineage in the developing heart," Nature, vol. 454, pp. 109-113 (2008).
U.S. Appl. No. 14/832,324, Jun. 9, 2017.
Chen, G. et al., "Chemically defined conditions for human iPS Cell derivation and culture," Nature Methods, vol. 8(5):424-429 (2011).
Gearing, D. et al., "Leukemia inhibitory factor receptor is structurally related to the IL-6 signal transducer, gp130," EMBO, vol. 10(10):2839-2848 (1991).
International Preliminary Report on Patentability, PCT/US2015/046309, dated Feb. 28, 2017, 11 pages.
International Search Report and Written Opinion, PCT/US2017/017952, dated May 3, 2017, 14 pages.
Keegan, K. et al., "Isolation of an additional member of the fibroblast growth factor receptor family, FGFR-3," Proc. Natl. Acad. Sci. USA, vol. 88(4):1095-1099 (1991).
Orchard, C., "T-tubule function in mammalian cardiac myocytes," Circ. Res., vol. 92(11):1182-1192 (2003).
Schiemann, W.P. et al., "Phosphorylation of the human leukemia inhibitory factor (LIF) receptor by mitogen-activated protein kinase and the regulation of LIF receptor function by heterologous receptor activation," Proc. Natl.. Acad. Sci. USA, vol. 92(12):5361-5365 (1995).
Shiang, R. et al., "Mutations in the transmembrane domain of FGFR3 cause the most common genetic form of dwarfism, achondroplasia," Cell, vol. 78:335-343 (1994).
U.S. Appl. No. 15/805,463, Jul. 17, 2018.
Masino, A. et al., "Transcriptional Regulation of Cardiac Progenitor Cell Populations," Circ Res., vol. 95:389-397 (2004).
International Search Report and Written Opinion, PCT/IB2017/001638, dated Mar. 22, 2018, 17 pages.
Lian, X. et al., "Directed cardiomyocyte differentiation from human pluripotent stem cells by modulating Wnt/?-catenin signaling under fully defined conditions," Nature Protocols, vol. 8(1):162-175 (2012).
Masuda S., et al., "Eliminating residual iPS cells for safety in clinical Application," Protein & Cell, vol. 6 (7):469-471 (2015).
Burridge, P., et al., "Chemically defined generation of human cardiomyocytes," Nature Methods, vol. 11 (8), pp. 855-860 (2014).
International Search Report and Written Opinion, PCT/2015/046309, dated Jan. 19, 2016, 19 pages.
U.S. Appl. No. 15/433,713, filed Feb. 15, 2017, Chuen Yan Leung.
U.S. Appl. No. 14/832,324, Dec. 16, 2016.
U.S. Appl. No. 14/832,324, filed Aug. 21, 2015, Kenneth R. Chien.
Badcock, G. et al., "The human embryonal carcinoma marker antigen TRA-1-60 is a sialylated keratan sulfate proteoglycan," Cancer Res., vol. 59:4715-4719 (1999).
Den Hartogh, S. et al., "A comprehensive gene expression analysis at sequential stages of in vitro cardiac differentiation from isolated MESP1-expressing-mesoderm progenitors," Scientific Reports, vol. 6 (19386) 16 pages (2016) doi: 10.1038/srep19386.
Fong, C. Y. et al., "Separation of SSEA-4 and TRA-1-60 labelled undifferentiated human embryonic stem cells from a heterogeneous cell population using magnetic-activated cell sorting (MACS) and fluorescence-activated cell sorting (FACS)," Stem Cell Rev., vol. 5:72-80 (2009).
Marrink, J. et al., "TRA-1-60: a new serum marker in patients with germ-cell tumors," Int. J. Cancer, vol. 49:368-372 (1991).
Menasche, P. et al., "Human embryonic stem cell-derived cardiac progenitors for severe heart failure treatment: first clinical case report," European Heart Journal, vol. 36:2011-2017 (2015).
Menon, V. et al., "Flow Cytometry Protocols for Surface and Intracellular Antigen Analyses of Neural Cell Types," J. Vis. Exp., vol. 94 (e52241) 11 pages (2014) doi:10.3791/52241.
Rodrigues, G. et al., "Purification of Human Induced Pluripotent Stem Cell-Derived Neural Precursors Using Magnetic Activated Cell Sorting," Methods in Molecular Biology, vol. 283:137-145 (2015).
Schopperle, W.M. et al., "The TRA-1-60 and TRA-1-81 human pluripotent stem cell markers are expressed on podocalyxin in embryonal carcinoma," Stem Cells, vol. 25:723-730 (2007).
Soh, B-S, et al. "Endothelin-1 supports clonal derivation and expansion of cardiovascular progenitors derived from human embryonic stem cells," Nature Communications, vol. 7 (10774) 10 pages (2016) doi: 10.1038/ncomms10774.
Bearzi, C. et al., "Human cardiac stem cells," PNAS, vol. 104 (35):14068-14073 (2007).
Molkentin and Houser, "Are Resident c-Kit+ Cardiac Stem Cells Really All That Are Needed to Mend a Broken Heart?," Circ Res., vol. 113:1037-1039 (2013).
Sandstedt, J. et al., "Human C-kit+CD45-cardiac stem cells are heterogeneous and display both cardiac and endothelial commitment by single-cell qPCR analysis," Biochemical and Biophysical Research Communications, vol. 443: 234-238 (2014).
Sultana, N. et al., "Resident c-kit+ cells in the heart are not cardiac stem cells," Nature Communications, vol. 6 (8701) 10 pages (2015).
Van Berlo, J. et al., "c-kit+ cells minimally contribute cardiomyocytes to the heart," Nature, vol. 509: 337-351 (2014).
U.S. Appl. No. 16/109,218, filed Aug. 22, 2018, Kenneth R. Chien.
U.S. Appl. No. 14/832,324, Nov. 30, 2018.
U.S. Appl. No. 15/433,713, Mar. 11, 2019.
U.S. Appl. No. 15/433,713, Nov. 7, 2018.
U.S. Appl. No. 15/805,463, Dec. 19, 2018.
Ardehali, R. et al., "Prospective isolation of human embryonic stem cell-derived cardiovascular progenitors that integrate into human fetal heart tissue," PNAS, vol. 110(9): 3405-3410 (2013).
Ardehali, R. et al., "Prospective isolation of human embryonic stem cell-derived cardiovascular progenitors that integrate into human fetal heart tissue," Supporting Information, PNAS, 12 pages (2013).
Chong, J. et al., "Human Embryonic Stem Cell-Derived Cardiomyocytes Regenerate Non-Human Primate Hearts," Nature, vol. 510(7504): 273-277 (2014).
Christoforou, N. et al., "Implantation of Mouse Embryonic Stem Cell-Derived Cardiac Progenitor Cells Preserves Function of Infarcted Murine Hearts," PLOS ONE, vol. 5(7):e11536, 14 pages (2010).
Gao, L. et al., "Myocardial Tissue Engineering With Cells Derived from Human Induced-Pluripotent Stem Cells and a Native-Like, High-Resolution, 3-Dimensionally Printed Scaffold," Circ Res., vol. 120(8): 1318-1325 (2017).
Gao, L. et al., "Supplemental Material Myocardial tissue engineering with cardiac cells derived from human induced-pluripotent stem cells and a native-like, high-resolution, 3-dimensionally printed scaffold," Circ Res., vol. 120(8):1318-1325 (2017).
Horvat, R. et al., "Endothelial Cell Membranes Contain Podocalyxin the Major Sialoprotein of Visceral Glomerular Epithelial Cells," The Journal of Cell Biology, vol. 102: 484-491 (1986).
International Preliminary Report on Patentability, PCT/US2017/017952, dated Aug. 21, 2018, 7 pages.
International Search Report and Written Opinion, PCT/IB2018/001026, dated Jan. 16, 2019, 13 pages.
Karakikes, I. et al., "Small molecule-mediated directed differentiation of human embryonic stem cells toward ventricular cardiomyocytes," Stem Cells Transl Med., vol. 3(1):18-31 (2014).
Kim, M.S., et al., "Activin-A and Bmp4 levels modulate cell type specification during CHIR-induced cardiomyogenesis," PLOS ONE, vol. 10(2):e01186701, 16 pages (2015).

(56) References Cited

OTHER PUBLICATIONS

Koyanagi, M. et al., "Differentiation of circulating endothelial progenitor cells to a cardiomyogenic phenotype depends on E-cadherin," FEBS Letters, vol. 579: 6060-6066 (2005).
Lian, Q. et al. "Establishing Clonal Cell Lines with Endothelial-Like Potential from CD9hi, SSEA-1-Cells in Embryonic Stem Cell-Derived Embryoid Bodies," PLOS One, Issue 1(1):e6, 10 pages (2006) doi:10.1371/journal.pone.0000006.
Masumoto, H. et al., "Human iPS cell-engineered cardiac tissue sheets with cardiomyocytes and vascular cells for cardiac regeneration," Scientific Reports, vol. 4 : 6716, 7 pages (2014).
Nazarov, I. et al., "Multipotent Stromal Stem Cells from Human Placenta Demonstrate High Therapeutic Potential," Stem Cells Translational Medicine, vol. 1: 359-372 (2012).
Parikh, A. et al., "Signaling Pathways and Gene Regulatory Networks in Cardiomyocyte Differentiation," Tissue Engineering: Part B. vol. 21(4):377-392 (2015).
Plein, A. et al., "Neural crest-derived SEMA3C activates endothelial NRP1 for cardiac outflow tract septation," Journa of Clinical Investigation, vol. 125 (7): 2661-2676 (2015).
Stepniewski, J. et al., "Induced pluripotent stem cells as a model for diabetes investigation," Scientific Reports, vol. 5 (8597): 14 pages (2015) DOI: 10.1038/srep08597.
Stevens, K.R. et al., "Physiological function and transplantation of scaffold-free and vascularized human cardiac muscle tissue," PNAS, vol. 106(39): 16568-16573 (2009).
Stevens, K.R. et al., "Physiological function and transplantation of scaffold-free and vascularized human cardiac muscle tissue," Supporting Information, PNAS, vol. 106(39): 5 pages (2009).
Yin, L. et a., "Induction of Vascular Progenitor Cells from Endothelial Cells Stimulates Coronary Collateral Growth," Circ Res., vol. 110(2): 241-252 (2012).
Andersson, E.R., et al., "Therapeutic modulation of Notch signalling—are we there yet?" Nat. Rev. Drug Discov. vol. 13, 357-378, (2014).
Barbash, I.M. et al. "Systemic delivery of bone marrow-derived mesenchymal stem cells to the infarcted myocardium: feasibility, cell migration, and body distribution," Circulation, vol. 108, pp. 863-868 (2003).
Basavarajaiah, S., et al., "Physiological upper limits of left ventricular dimensions in highly trained junior tennis players" Br. J. Sports Med., vol. 41(11), 784-788. (2007).
Bash, J. et al., "ReVNF-kappaB can trigger the Notch signaling pathway by inducing the expression of Jagged1, a ligand for Notch receptors," The EMBO Journal, vol. 18(10) pp. 2803-2811 (1999).
Bergmann, O., et al., "Dynamics of Cell Generation and Turnover in the Human Heart," Cell, vol. 161(17), pp. 1566-1575 (2015).
Bergmann, O., et al., "Evidence for cardiomyocyte renewal in humans," Science, vol. 324(5923), pp. 98-102 (2009).
Birket, M. et al., "Expansion and patterning of cardiovascular progenitors derived from human pluripotent stem cells," Nature Biotechnology, vol. 33(9), pp. 970-979 (2015).
Bittira, B. et al., "Mobilization and homing of bone marrow stromal cells in myocardial infarction," Eur. J. Cardiothorac. Surg., vol. 24(3) pp. 393-398 (2003).
Blin, G. et al., "A purified population of multipotent cardiovascular progenitors derived from primate pluripotent stem cells engrafts in postmyocardial infarcted nonhuman primates," The Journal of Clinical Investigation, vol. 120(4) pp. 1125-1139 (2010).
Brette, F., et al., "T-tubule function in mammalian cardiac myocytes," Circulation Research, vol. 92(11) pp. 1182-1192 (2003).
Bu, L., et al., "Human ISL1 heart progenitors generate diverse multipotent cardiovascular cell lineages," Nature, vol. 460, pp. 113-117 (2009).
Bui, A.L. et al., "Epidemiology and risk profile of heart failure," Nat. Rev. Cardiol, vol. 8(1) pp. 30-41 (2011).
Buikema, J. et al., "Wnt/beta-catenin signaling directs the regional expansion of first and second heart field-derived ventricular cardiomyocytes," Development, vol. 140, pp. 4165-4176 (2013).

Cai, C.L. et al., "Isl1 identifies a cardiac progenitor population that proliferates prior to differentiation and contributes a majority of cells to the heart," Developmental Cell, vol. 5, pp. 877-889 (2003).
Campagnolo, P. et al., "c-Kit+ progenitors generate vascular cells for tissue-engineered grafts through modulation of the Wnt/Ktf4 pathway," Biomaterials, vol. 60, pp. 53-61 (2015).
Chong, J. et al., "Human embryonic-stem-cell-derived cardiomyocytes regenerate non-human primate hearts," Nature, vol. 510, pp. 273-277, (2014).
Conradi, L.,et al. "Immunobiology of fibrin-based engineered heart tissue," Stem Cells Transl. Med., vol. 4(6), pp. 625-631 (2015).
Di Giorgio, F.P. et al., "Human embryonic stem cell-derived motor neurons are sensitive to the toxic effect of glial cells carrying an ALS-causing mutation," Cell Stem Cell, vol. 3, pp. 637-648 (2008).
Domian, I.J., et al., "Generation of functional ventricular heart muscle from mouse ventricular progenitor cells," Science vol. 326(5951),pp. 426-429 (2009).
Elliot, D. et al., " NKX2-5eGFP/w hESCs for isolation of human cardiac progenitors and cardiomyocytes," Nature Methods, vol. 8(12), pp. 1037-1043 (2011).
Fernandes, S. et al., "Comparison of Human Embryonic Stem Cell-Derived Cardiomyocytes, Cardiovascular Progenitors, and Bone Marrow Mononuclear Cells for Cardiac Repair," Stem Cell Reports, vol. 5, pp. 753-762 (2015).
Forbes, S.J. et al., "Preparing the ground for tissue regeneration: from mechanism to therapy," Nat. Med., vol. 20(8), pp. 857-869 (2014).
Gaetani, R., et al., "Epicardial application of cardiac progenitor cells in a 3D-printed gelatin/hyaluronic acid patch preserves cardiac function after myocardial infarction," Biomaterials, vol. 61, 339-348. (2015).
Gama-Carvalho, M., et al., "Regulation of Cardiac Cell Fate by microRNAs: Implications for Heart Regeneration," Cells, vol. 3(4), pp. 996-1026 (2014).
Giordano, F.J., et al., "A cardiac myocyte vascular endothelial growth factor paracrine pathway is required to maintain cardiac function," PNAS,. U. S. A., vol. 98(10), pp. 5780-5785 (2001).
Guo, Y. et al, "Targeted deletion of the A3 adenosine receptor confers resistance to myocardial ischemic injury and does not prevent early preconditioning," J Mol Cell Cardiol., vol. 33(4), pp. 825-830 (2001).
Harrison, R.H., et al., "Tissue engineering and regenerative medicine: a year in review," Tissue Eng. Part B., vol. 20, 1-16. (2014).
Headrick, J.P, et al., "Acute adenosinergic cardioprotection in ischemic-reperfused hearts," American Journal of Physiology Heart and Circulatory Physiology, vol. 285, pp. H1797-H1818, (2003).
High, F. et al., "Endothelial expression of the Notch ligand Jagged1 is required for vascular smooth muscle development," Proceedings of the National Academy of Sciences of the United States of America, vol. 105(6), pp. 1955-1959 (Feb. 2008).
Huang, J. et al., "Tissue Engineering and Regenerative Medicine in Basic Research: A Year in Review 2014," Tissue Engineering: Part B, vol. 21(2) pp. 1-11 (2015).
Invitation to Pay Additional Fees and, where applicable, Protest Fee, PCT/US2015/046309, dated Nov. 6, 2015, pp. 1-7.
Jackson, K.A. et al., "Regeneration of ischemic cardiac muscle and vascular endothelium by adult stem cells," J. Clin. Invest., vol. 107(11), pp. 1395-1402 (2001).
Jones, E.A. et al."JAGGED1 expression in human embryos: correlation with the Alagille syndrome phenotype," J. Med. Genet. vol. 37, pp. 658-662 (2000).
Kaiser, N.J., et al., "Physiologically inspired cardiac scaffolds for tailored in vivo function and heart regeneration," Biomed. Mater. vol. 10(3) 034003. (2015).
Khan, M., et al., "Evaluation of Changes in Morphology and Function of Human Induced Pluripotent Stem Cell Derived Cardiomyocytes (HiPSC-CMs) Cultured on an Aligned-Nanofiber Cardiac Patch," PLoS One 10, e0126338, 19 pages, (2015).
Kirikoshi, H., et al."Molecular cloning and characterization of human Frizzled-4 on chromosome 11q14-q21," Biochem. Biophys. Res. Commun., vol. 264(3), pp. 955-961(1999).
Koo, B.-K., et al.,"Controlled gene expression in primary Lgr5 organoid cultures," Nat. Methods vol. 9(1),pp. 81-83 (2012).

(56) References Cited

OTHER PUBLICATIONS

Kraehenbuehl, T.P, et al., "Three-dimensional biomaterials for the study of human pluripotent stem cells," Nat. Methods vol. 8(9), pp. 731-736. (2011).

Krishnan, A, et al., "A detailed comparison of mouse and human cardiac development," Pediatr. Research, vol. 76(6) pp. 500-507 (2014).

Kwon, C. et al., "Canonical Wnt signaling is a positive regulator of mammalian cardiac progenitors," PNAS, USA, vol. 104(26),pp. 10894-10899 (2007).

Laflamme, M.A., et al., "Cardiomyocytes derived from human embryonic stem cells in pro-survival factors enhance function of infarcted rat hearts," Nat. Biotechnol., vol. 25(9), pp. 1015-1024 (2007).

Laflamme, M.A., et al., "Formation of human myocardium in the rat heart from human embryonic stem cells." Am. J. Pathol. vol. 167(3)pp. 663-671 (2005).

Laflamme, M.A., et al., "Heart regeneration," Nature, vol. 473(7347) pp. 326-335 (2011).

Lalit, P. et al., "Induced Pluripotent Stem Cells for Post-Myocardial Infarction Repair, Remarkable Opportunities and Challenges," Circulation Research, vol. 114, pp. 1328-1345 (2014).

Lancaster, M.A., et al., "Cerebral organoids model human brain development and microcephaly," Nature, vol. 501(7467), pp. 373-379, (2013).

Laugwitz, K.-L., et al., "Postnatal isl1+ cardioblasts enter fully differentiated cardiomyocyte lineages," Nature 433, 647-653. (2005).

Li, L. et al., The human homolog of rat Jagged1 expressed by marrow stroma inhibits differentiation of 32D cells through interaction with Notch1, Immunity, vol. 8(1) pp. 43-55 (1998).

Li, L., et al., "Alagille syndrome is caused by mutations in human Jagged1, which encodes a ligand for Notch1," Nat. Genet., vol. 16, 243-251.(1997).

Lian, X. et al., "Directed cardiomyocyte differentiation from human pluripotent stem cells by modulating Wnt/[beta]-catenin signaling under fully defined conditions," Nature Protocols, vol. 8(1), pp. 162-175 (Dec. 20, 2012).

Lian, X., et al., "Insulin inhibits cardiac mesoderm, not mesendoderm, formation during cardiac differentiation of human pluripotent stem cells and modulation of canonical wnt signaling can rescue this inhibition," Stem Cells, vol. 31(3), pp. 447-457. (2013).

\* cited by examiner

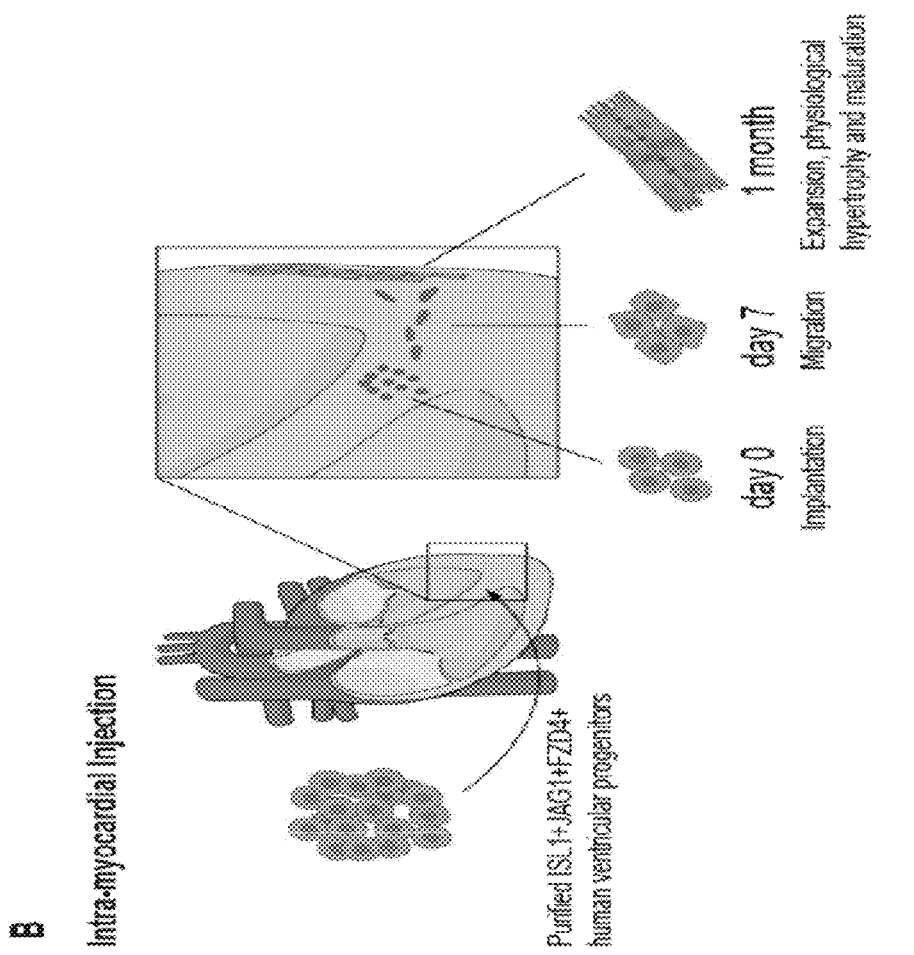
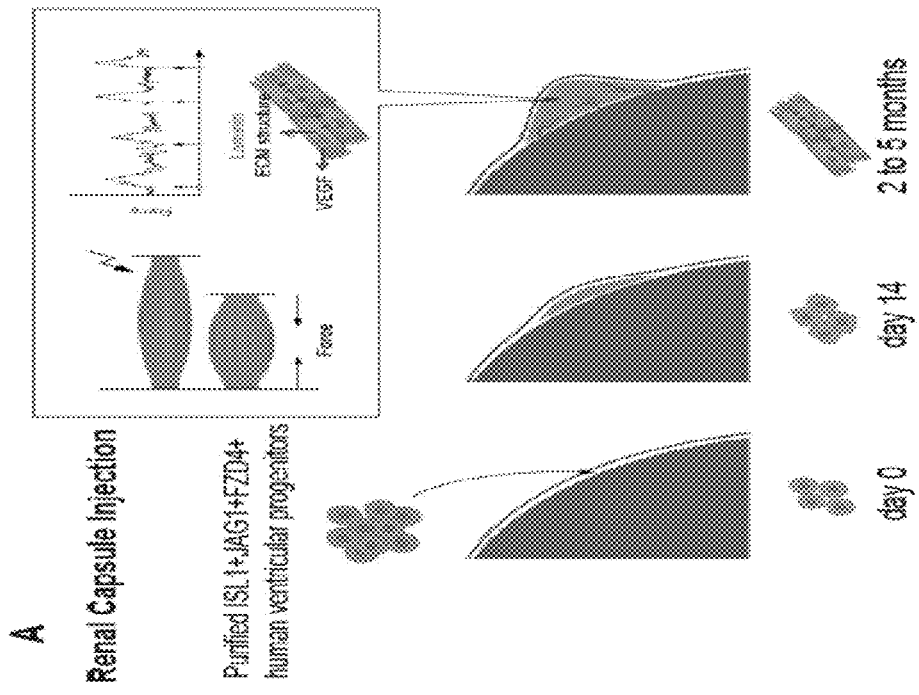

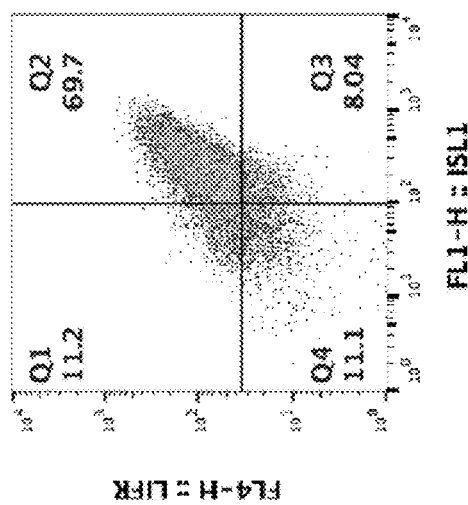
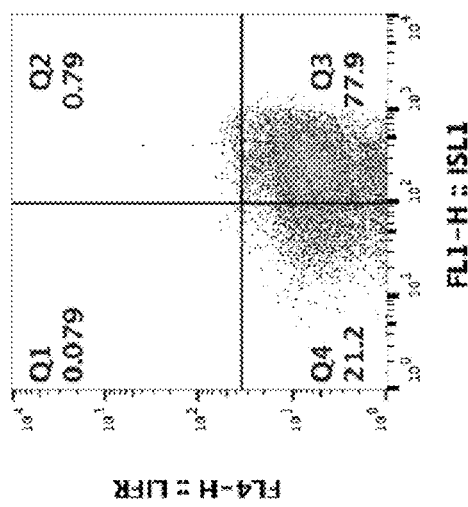
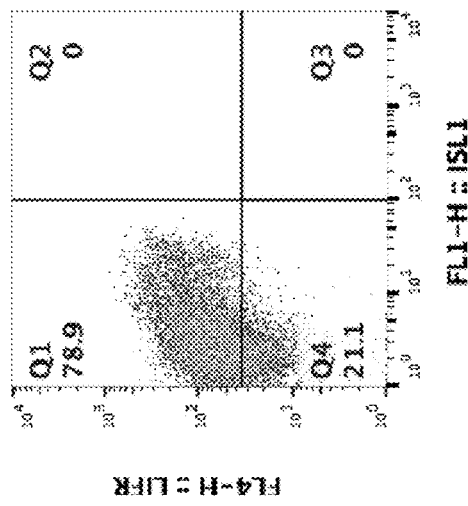
Fig. 9

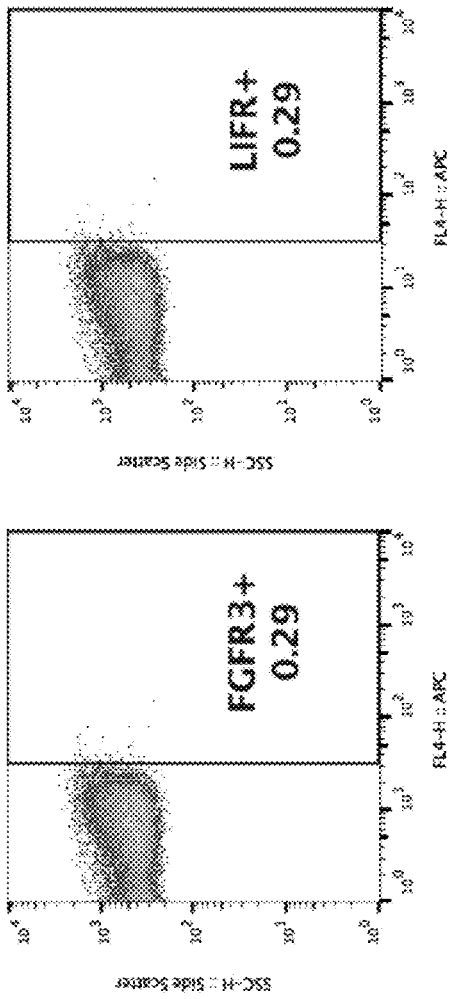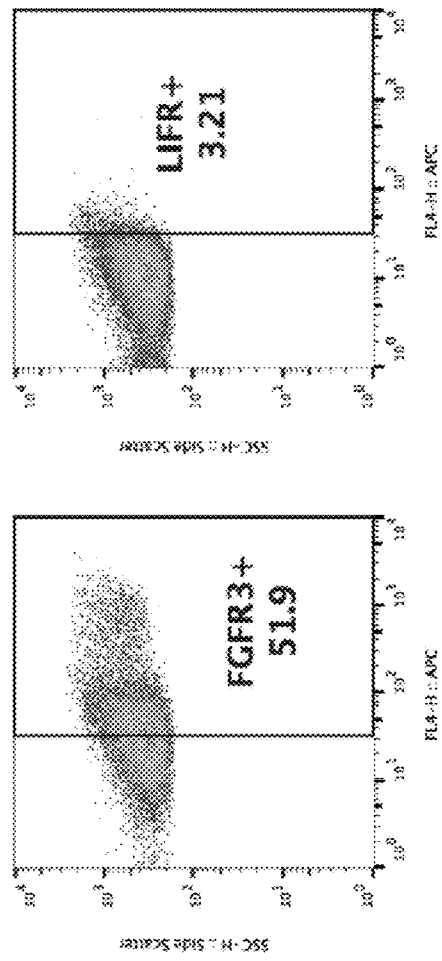
Fig. 10A

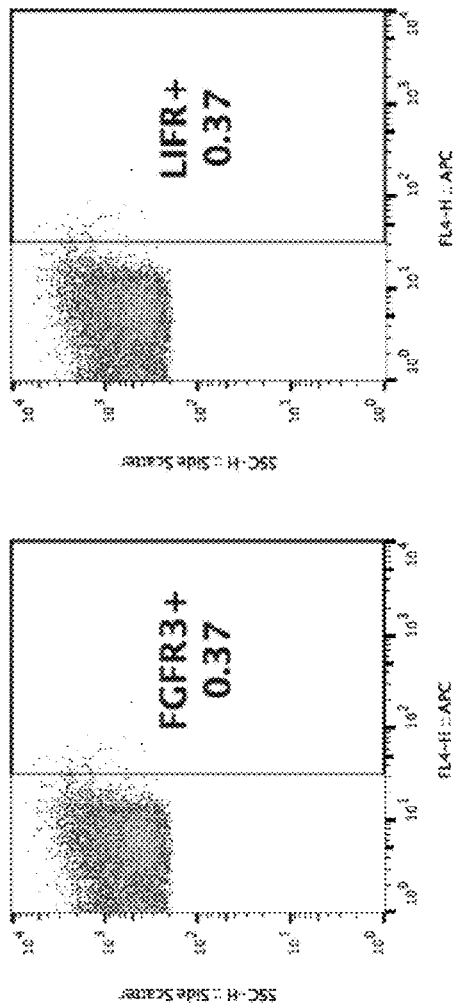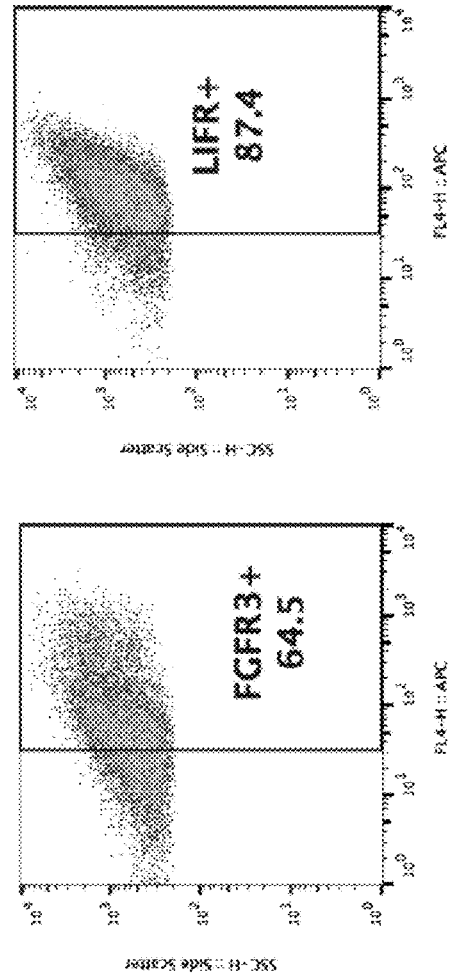
Fig. 10B

USE OF LIFR OR FGFR3 AS A CELL SURFACE MARKER FOR ISOLATING HUMAN CARDIAC VENTRICULAR PROGENITOR CELLS

RELATED APPLICATIONS

This application is a continuation in part of U.S. Ser. No. 14/832,324, filed on Aug. 21, 2015, which claims the benefit of the priority date of U.S. Provisional Application No. 62/040,892, filed on Aug. 22, 2014, and U.S. Provisional Application No. 62/194,016, filed on Jul. 17, 2015. The content of these applications is hereby incorporated by reference in its entirety.

BACKGROUND OF THE INVENTION

Heart failure, predominantly caused by myocardial infarction, is the leading cause of death in both adults and children worldwide and is increasing exponentially worldwide (Bui, A. L. et al. (2011) *Nat. Rev. Cardiol.* 8:30-41). The disease is primarily driven by the loss of ventricular muscle that occurs during myocardial injury (Lin, Z. and Pu, W. T. (2014) *Sci. Transl. Med.* 6:239rv1) and is compounded by the negligible ability of the adult heart to mount a regenerative response (Bergmann, O. et al. (2009) *Science* 324: 98-102; Senyo, S. E. et al. (2013) *Nature* 493:433-436). Although heart transplantation can be curative, the markedly limited availability of human heart organ donors has led to a widespread unmet clinical need for a renewable source of pure, mature and functional human ventricular muscle tissue (Segers, V. F. M. and Lee, R. J. (2008) *Nature* 451:937-942; Spater, D. et al. (2014) *Development* 141:4418-4431).

Human pluripotent stem cells (hPSCs) offer the potential to generate large numbers of functional cardiomyocytes for potential clinical restoration of function in damaged or diseased hearts. Transplantation of stem cells into the heart to improve cardiac function and/or to enrich and regenerate damaged myocardium has been proposed (see e.g., U.S. Patent Publication 20040180043). Combination therapy, in which adult stem cells are administered in combination with treatment with growth factor proteins has also been proposed (see e.g., U.S. Patent Publication 20050214260).

While cell transplantation into the heart offers a promising approach for improving cardiac function and regenerating heart tissue, the question of what type(s) of cells to transplant has been the subject of much investigation. Types of cells investigated for use in regenerating cardiac tissue include bone marrow cells (see e.g., Orlic, D. et al. (2001) *Nature* 410:701-705; Stamm, C. et al. (2003) *Lancet* 361: 45-46; Perin, E. C. et al. (2003) *Circulation* 107:2294-2302), adult stem cells (see e.g., Jackson, K. A. et al. (2001) *J. Clin. Invest.* 107:1395-1402), bone marrow-derived mesenchymal stem cells (see e.g., Barbash, I. M. et al. (2003) *Circulation* 108:863; Pettinger, M. F. and Martin, B. J. (2003) *Circ. Res.* 95:9-20), bone marrow stromal cells (Bittira, B. et al. (2003) *Eur. J. Cardiothorac. Surg.* 24:393-398), a combination of mesenchymal stem cells and fetal cardiomyocytes (see e.g., Min, J. Y. et al. (2002) *Ann. Thorac. Surg.* 74:1568-1575) and a combination of bone marrow-derived mononuclear cells and bone marrow-derived mesenchymal stem cells (see e.g., U.S. Patent Publication 20080038229). Dedifferentiation of adult mammalian cardiomyocytes in vitro to generate cardiac stem cells for transplantation has also been proposed (see e.g., U.S. Patent Publication 20100093089).

A significant advancement in the approach of cell transplantation to improve cardiac function and regenerate heart tissue was the identification and isolation of a family of multipotent cardiac progenitor cells that are capable of giving rise to cardiac myocytes, cardiac smooth muscle and cardiac endothelial cells (Cal, C. L. et al. (2003) *Dev. Cell.* 5:877-889; Moretti, A. et al. (2006) *Cell* 127:1151-1165; Bu, L. et al. (2009) *Nature* 460:113-117; U.S. Patent Publication 20060246446). These cardiac progenitor cells are characterized by the expression of the LIM homeodomain transcription factor Islet 1 (Isl1) and thus are referred to as Isl1+ cardiac progenitor cells. (Ibid). In contrast, Isl1 is not expressed in differentiated cardiac cells. Additional markers of the Isl1+ cardiac progenitor cells that arise later in differentiation than Isl1 have been described and include Nkx2.5 and flk1 (see e.g., U.S. Patent Publication 20100166714).

The renewal and differentiation of Isl1+ cardiac progenitor cells has been shown to be regulated by a Wnt/beta-catenin signaling pathway (see e.g., Qyang, Y. et al. (2007) *Cell Stem Cell.* 1:165-179; Kwon, C. et al. (2007) *Proc. Natl. Acad. Sci. USA* 104:10894-10899). This has led to the development of methods to induce a pluripotent stem cell to enter the Isl1+ lineage and for expansion of the Isl1+ population through modulation of Wnt signaling (see e.g., Lian, X. et al. (2012) *Proc. Natl. Acad. Sci. USA* 109:E1848-57; Lian, X. et al. (2013) *Nat. Protoc.* 8:162-175; U.S. Patent Publication 20110033430; U.S. Patent Publication 20130189785).

While human pluripotent stem cells hold great promise, a significant challenge has been the ability to move from simply differentiation of diverse cardiac cells to forming a larger scale pure 3D ventricular muscle tissue in vivo, which ultimately requires vascularization, assembly and alignment of an extracellular matrix, and maturation. Toward that end, a diverse population of cardiac cells (atrial, ventricular, pacemaker) has been coupled with artificial and decellurized matrices (Masumoto, H. et al. (2014) *Sci. Rep.* 4:5716; Ott, H. C. et al. (2008) *Nat. Med.* 14:213-221; Schaaf, S. et al. (2011) *PLoS One* 6:e26397), vascular cells and conduits (Tulloch, N. L. et al. (2011) *Circ. Res.* 109:47-59) and cocktails of microRNAs (Gama-Garvalho, M. et al. (2014) *Cells* 3:996-1026) have been studies, but the goal remains elusive.

While the identification of Isl1 as a marker of cardiac progenitor cells was a significant advance, since Isl1 is an intracellular protein it is not a suitable marker for use in isolating large quantities of viable cells. Rather, a cell surface marker(s) is still needed. Furthermore, Isl1 as a marker identifies a population that can differentiate into multiple cell types within the cardiac lineage, and thus there is still a need for markers that identify cardiac progenitor cells that are biased toward a particular cell type within the cardiac lineage, in particular for progenitor cells that differentiate into ventricular cells. Accordingly, there is still a great need in the art for additional markers of cardiac progenitor cells, in particular cell-surface markers of cardiac progenitor cells, that predominantly give rise to cardiomyocytes and that would allow for rapid isolation and large scale expansion of cardiomyogenic progenitor cells. Furthermore, there is still a great need in the art for methods and compositions for isolating cardiac ventricular progenitors, which differentiate into ventricular muscle cells in vivo, thereby allowing for transplantation of ventricular progenitors or ventricular muscle cells in vivo to enhance cardiac function.

SUMMARY OF THE INVENTION

This invention describes the use of Leukemia Inhibitory Factor Receptor (LIFR) or Fibroblast Growth Factor Receptor 3 (FGFR3) as a cell surface marker for isolating human cardiac progenitor cells. Furthermore, these human cardiac progenitor cells are biased toward the ventricular lineage such that they differentiate predominantly into ventricular muscle cells both in vitro and in vivo. That is, these cardiac progenitor cells can be cultured under conditions in vitro such that they are biased toward the ventricular lineage and thus are human ventricular progenitor (HVP) cells. Moreover, when introduced into the ventricular region of the heart in a subject, these progenitor cells differentiate almost exclusively into ventricular muscle cells that function according to their ventricular programming. In particular, the human ventricular progenitor cells provided herein utilize a cell autonomous pathway by which these cells can build a pure 3-D vascularized, functional and mature ventricular cell wall in vivo on the surface of normal murine kidney or heart, thereby allowing for organ-on-organ in vivo tissue engineering.

Using Islet 1 (ISL1) as a marker, a scalable two-step culture protocol for generating HVPs has been developed and cell surface markers (LIFR/FGFR3) have been identified that allow the generation and purification of billions of pure HVPs from human pluripotent stem cells (hPSCs). These HVPs can also be identified in the 4 week human fetal heart ventricular chambers.

Transplantation of the ventricular progenitor cells provided herein produces a pure, functional and mature human ventricular muscle organ of large size (e.g., twice the size of the murine heart) that can generate force, respond to catecholamines, lose automaticity, contain T tubules and display hypertrophic growth of adult rod-shaped cells by 5 months post-transplantation. Thus, human ventriculogenesis can be achieved via a cell autonomous pathway driven by the purified ISL1/LIFR/FGFR3 human ventricular progenitors provided herein. These HPVs provided herein allow for new in vivo models of human cardiac disease in murine-human chimeras and for the development of organ-on-organ regenerative therapeutic strategies for cardiac disease.

This identification of a key cell surface marker of cardiac ventricular progenitor cells allows for easy and rapid isolation of the cells. Furthermore, determination of culture conditions for expansion and ventricular lineage bias of the cells allows for the preparation of large cultures (a billion or more cells) of a clonal population of cardiac ventricular progenitor cells. These cells can be used, for example, to improve function in a damaged heart in a subject, particularly damage in the ventricular region. The progenitor cells can be transplanted in vivo for differentiation into ventricular cells in situ or, alternatively, a heart muscle patch, comprising ventricular muscle cells, can be prepared in vitro from the progenitors for subsequent transplantation in vivo. The cells also can be used, for example, in in vitro toxicity screening assays to evaluate the cardiac toxicity of test compounds, as well as for biochemical studies to identify relevant pathways used in cardiac maturation and differentiation.

Thus, the invention provides for the first time human cardiac ventricular progenitor cells in purified form. The human cardiac ventricular progenitors are capable of differentiation into ventricular muscle cells in vitro and in vivo. These progenitor cells can be expanded to large numbers of cells in vitro and when transplanted into the ventricular region of the heart in vivo they differentiate essentially exclusively into ventricular muscle cells. Still further, the cells have the capacity to migrate in vivo to different sites and, when transplanted in vivo the cells does what they are programmed to do as a ventricular cell (as opposed to a cardiac myocyte which simply contracts). Thus, the ventricular progenitor cells can be grafted to native tissue to enhance ventricular function and have the ability to call in vasculature into the new ventricular tissue.

Using the RNA-seq technique combined with a robust cardiac differentiation protocol, transcriptional expression at a genome-scale level at different time points of hPSC differentiation was performed. These experiments led to the identification of Leukemia Inhibitory Factor Receptor (LIFR) and Fibroblast Growth Factor Receptor 3 (FGFR3) as cell surface markers for Isl1+ cardiomyogenic progenitor cells derived from hPSCs. Co-expression of Isl1 and LIFR, or Isl1 and FGFR3, on cardiomyogenic progenitor cells in vitro was demonstrated. Still further, after transplantation of purified human cardiomyogenic progenitor cells into normal or injured hearts in mice, enriched human cardiomyogenic progenitor cells gave rise to cTnT+ cardiomyocytes demonstrating the cardiomyogenic nature of the progenitor cells. In these in vivo transplantation studies, larger grafts were observed in the injured hearts transplanted with the cardiomyogenic progenitor cells, as compared to normal hearts, demonstrating the capacity of the cardiomyogenic progenitor cells for cardiomyocyte regeneration.

Still further, the RNA-seq experiments identified additional potential surface markers, including the following markers for mesoderm cells expressing brachyury: FZD10, CD48, CDID, CD8B, IL15RA, TNFRSF1B, TNFSF13, ICOSLG, SEMA7A, SLC3A2, SDC1 and HLA-A; and the following markers for cardiac mesoderm mespl positive cells: CXCR4, ANPEP, ITGA5, TNFRSF9, FZD2, CDID, CD177, ACVRL1, ICAM1, LICAM, NGFR, ABCG2, FZD7, TNFRSF13C and TNFRSF1B; and the following markers for cardiac progenitor cells: PDGFRA, Jagged 1 (JAG1), TNFSF9 and Frizzled 4 (FZD4). Any of these additional cardiac progenitor markers can be used in the methods of the invention to isolate progenitors at different stages of differentiation. In particular, the cardiac progenitor markers PDGFRA, JAG1, TNFSF9 or FZD4 can be used in a similar manner to LIFR and FGFR3, as described herein, for isolation of cardiomyogenic progenitors.

Accordingly, in one aspect, the invention pertains to a method for isolating human cardiac ventricular progenitor cells, the method comprising:

contacting a culture of cells containing human cardiac progenitor cells with one or more agents reactive with LIFR and/or FGFR3; and separating LIFR and/or FGFR3 reactive positive cells from non-reactive cells to thereby isolate human cardiac ventricular progenitor cells.

In one embodiment, the human cardiac progenitor cells are contacted both with an agent reactive with LIFR and with an agent reactive with FGFR3 to thereby separate LIFR and FGFR3 reactive positive cells from non-reactive cells.

Preferably, the human cardiac progenitor cells are Islet 1+ human cardiac progenitor cells. In another embodiment, the culture of cells is also contacted with an agent reactive with Islet 1; and LIFR reactive/Islet 1 reactive positive cells, or FGFR3 reactive/Islet 1 reactive cells, are separated from non-reactive cells to thereby isolate cardiac ventricular progenitor cells. The culture of cells can be simultaneously contacted with the agent reactive with LIFR and/or FGFR3 and the agent reactive with Islet 1. Alternatively, the culture of cells can be contacted with the agent reactive with Islet 1 before contacting with the agent reactive with LIFR and/or FGFR3. Alternatively, the culture of cells can be contacted with the agent reactive with LIFR and/or FGFR3 before contacting with the agent reactive with Islet 1. In another embodiment, the human cardiac ventricular progenitor cells are further cultured and differentiated such that they express the ventricular marker MLC2v.

In another aspect, the invention pertains to a method for isolating human cardiac ventricular progenitor cells, the method comprising:

culturing human pluripotent stem cells under conditions that generate cardiac progenitor cells to obtain a cultured cell population;

contacting the cultured cell population with one or more agents reactive with LIFR and/or FGFR3; and separating LIFR and/or FGFR3 reactive positive cells from non-reactive cells to thereby isolate human cardiac ventricular progenitor cells.

In one embodiment, the human cardiac progenitor cells are contacted both with an agent reactive with LIFR and with an agent reactive with FGFR3 to thereby separate LIFR and FGFR3 reactive positive cells from non-reactive cells.

In one embodiment, the culture of cells is also contacted with an agent reactive with Islet 1; and LIFR reactive/Islet 1 reactive positive cells, or FGFR3 reactive/Islet 1 reactive positive cells, are separated from non-reactive cells to thereby isolate human cardiac ventricular progenitor cells. The culture of cells can be simultaneously contacted with the agent(s) reactive with LIFR and/or FGFR3 and the agent reactive with Islet 1. Alternatively, the culture of cells can be contacted with the agent reactive with Islet 1 before contacting with the agent(s) reactive with LIFR and/or FGFR3. Alternatively, the culture of cells can be contacted with the agent(s) reactive with LIFR and/or FGFR3 before contacting with the agent reactive with Islet 1. In another embodiment, the human cardiac ventricular progenitor cells are further cultured and differentiated such that they express the ventricular marker MLC2v.

In the methods for isolating human cardiac ventricular progenitor cells, various types of agents that bind to LIFR or FGFR3 can be used as the agent(s) reactive with LIFR or FGFR3. For example, in one embodiment, the agent reactive with LIFR or FGFR3 is an anti-LIFR antibody or an anti-FGFR3 antibody, such as a monoclonal antibody. In another embodiment, the agent reactive with LIFR or FGFR3 is a soluble LIFR ligand or FGFR3 ligand, such as a LIFR ligand fusion protein or a FGFR3 ligand fusion protein. For example, the agent reactive with LIFR can comprise the LIFR ligand leukemia inhibitor factor (LIF), such as a soluble LIF fusion protein (e.g., a LIF/Ig fusion protein). Similarly, the agent reactive with FGFR3 can comprise the FGFR3 ligand fibroblast growth factor (FGF), such as a soluble FGF fusion protein (e.g., a FGF/Ig fusion protein).

In the methods for isolating human cardiac ventricular progenitor cells, various types of separation methods can be used to separate LIFR and/or FGFR3 reactive positive cells (or LIFR/Islet 1 or FGFR3/Islet 1 reactive positive cells) from non-reactive cells. For example, in one embodiment, the reactive positive cells are separated from the non-reactive cells by fluorescence activated cell sorting (FACS). In another embodiment, the reactive positive cells are separated from the non-reactive cells by magnetic activated cells sorting (MACS).

In yet another aspect, the invention pertains to a method of obtaining a clonal population of human cardiac ventricular progenitor cells, the method comprising:

isolating a single LIFR+ and/or FGFR3+ human cardiac ventricular progenitor cell; and culturing the single LIFR+ and/or FGFR3+ human cardiac ventricular progenitor cell under conditions such that the cell is expanded to at least $1 \times 10^9$ cells to thereby obtain a clonal population of human cardiac ventricular progenitor cells.

In one embodiment, the single LIFR+ and/or FGFR3+ human cardiac ventricular progenitor cell is Islet 1 positive, Nkx2.5 negative and flk1 negative at the time of initial culture. The single LIFR+ or FGFR3+ human cardiac ventricular progenitor cell can be isolated by methods such as those described above (e.g., FACS or MACS). The single LIFR+ and/or FGFR3+ human cardiac ventricular progenitor cell can be isolated using a reagent(s) reactive with LIFR and/or FGFR3, such as those described above (e.g., anti-LIFR antibodies, anti-FGFR3 antibodies, soluble LIFR ligands or soluble FGFR3 ligands, such as ligand fusion proteins). Upon further culture and differentiation, the clonal population of human cardiac ventricular progenitor cells can express the ventricular marker MLCV2.

In a preferred embodiment, the single LIFR+ and/or FGFR3+ human cardiac ventricular progenitor cell is cultured in vitro under conditions such that the cell is biased toward ventricular differentiation. For example, the single LIFR+ and/or FGFR3+ human cardiac ventricular progenitor cell can be cultured in Cardiac Progenitor Culture (CPC) medium (80% advanced DMEM/F12 supplemented with 20% KnockOut Serum Replacement, 2.5 mM GlutaMax and 100 µg/ml Vitamin C), which allows for differentiation of the cells into ventricular cells expressing the MLC2v ventricular marker. In various embodiments, the single LIFR+ and/or FGFR3+ human cardiac ventricular progenitor cell is expanded to a clonal population of, for example, at least $1 \times 10^9$ cells, at least $2 \times 10^9$ cells, at least $5 \times 10^9$ cells or at least $10 \times 10^9$ cells.

Accordingly in another aspect, the invention pertains to a clonal population of isolated LIFR+ and/or FGFR3+ human cardiac ventricular progenitor cells. In various embodiments, this clonal population comprises, for example, at least $1 \times 10^9$ cells, at least $2 \times 10^9$ cells, at least $5 \times 10^9$ cells or at least $10 \times 10^9$ cells. In a preferred embodiment, this clonal population comprises at least $1 \times 10^9$ LIFR+ human cardiac ventricular progenitor cells or at least $1 \times 10^9$ FGFR3+ human cardiac ventricular progenitor cells.

In yet another aspect, the invention pertains to a method of enhancing cardiac function in a subject using the LIFR+ and/or FGFR3+ human cardiac ventricular progenitor cells described herein. For example, in one embodiment, the invention provides a method of enhancing cardiac function in a subject, the method comprising administering a pharmaceutical composition comprising a clonal population LIFR+ and/or FGFR3+ human cardiac ventricular progenitor cells, such as a clonal population of at least at least $1 \times 10^9$ cells, at least $2 \times 10^9$ cells, at least $5 \times 10^9$ cells or at least $10 \times 10^9$ cells. In one embodiment, the clonal population is administered directly into the heart of the subject. For example, the clonal population can be administered directly into a ventricular region of the heart of the subject. In one embodiment, the pharmaceutical composition administered to the subject comprises the clonal population formulated onto a three dimensional matrix, such as a heart muscle patch comprising ventricular muscle cells. The subject is one in need of enhancement of cardiac function, for example someone who has suffered a myocardial infarction or someone who has a congenital heart disorder.

In yet another aspect, the invention pertains to a method for generating human ventricular tissue comprising
transplanting LIFR+ and/or FGFR3+ human cardiac ventricular progenitor cells into an organ of a non-human animal; and
allowing the progenitor cells to grow in vivo such that human ventricular tissue is generated.

The non-human animal can be, for example, an immunodeficient mouse. The organ can be, for example, the kidney (e.g., the cells are transplanted under the kidney capsule) or the heart. In one embodiment, the cells are transplanted at a time when one, two, three, four or five of the following cell marker patterns are present: (i) after peak of cardiac mesoderm formation; (ii) at time of peak Islet-1 expression; (iii) before peak of NKX2.5 expression; (iv) before peak expression of downstream genes MEF-2 and TBX-1; and (v) before expression of differentiated contractile protein genes. In one embodiment, the cells are transplanted between day 5 and day 7 (inclusive) of in vitro culture of human pluripotent stem cells under conditions to generate human ventricular progenitor cells. In another embodiment, the cells are transplanted on day 6 of in vitro culture of human pluripotent stem cells under conditions to generate human ventricular progenitor cells. The method can further include harvesting the human ventricular tissue generated in the non-human animal.

In still another aspect of the invention, the human cardiac ventricular progenitor cells described herein can be used in screening assays to evaluate the cardiac toxicity of a test compound. Accordingly, the invention provides a method of screening for cardiac toxicity of test compound, the method comprising providing LIFR+ and/or FGFR3+ cardiac ventricular progenitor cells;
contacting the cells with the test compound; and
measuring toxicity of the test compound for the cells,
wherein toxicity of the test compound for the cells indicates cardiac toxicity of the test compound. The toxicity of the test compound for the cells can be measured, for example, by assessing cell viability or other physiological parameters of the cell.

Culturing methods for generating human ventricular progenitor cells are also provided. For example, in one embodiment, the invention pertains to a method of generating human ventricular progenitors (HVPs) comprising:
culturing human pluripotent stems cells (hPSCs) in a medium comprising CHIR98014 such that cells expressing cardiac mesodermal markers are generated, and
culturing the cells expressing cardiac mesodermal markers in a medium comprising Wnt-059 such that HVPs are generated.

Other features and advantages of the invention will be apparent from the following detailed description and claims.

BRIEF DESCRIPTION OF THE DRAWINGS

FIGS. 8A-B is a schematic diagram of the transplantation of HPVs into the renal capsule (FIG. 8A) or intra-myocardially (FIG. 8B) for organ-on-organ tissue engineering.

FIG. 9 shows the results of double staining flow cytometry analysis of human ventricular progenitor (HVP) cells, showing coexpression of Isl1 and LIFR on the cells.

FIGS. 10A-B show the results of flow cytometry analysis of the expression of LIFR and FGFR3 on human ventricular progenitor cells (FIG. 10B) as compared to undifferentiated embryonic stem (ES) cells (FIG. 10A).

DETAILED DESCRIPTION OF THE INVENTION

Figure 1:
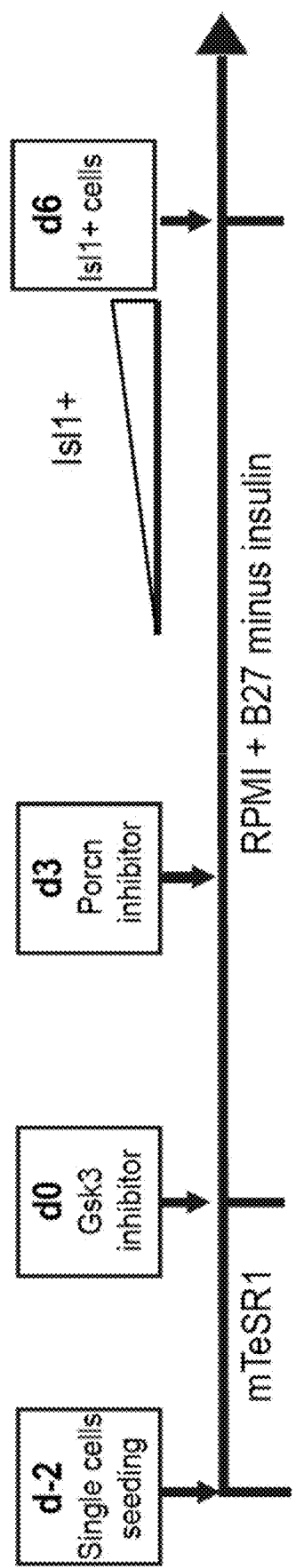
FIG. 1 is a schematic diagram of an exemplary culturing protocol for generating human Isl1+cardiomyogenic progenitor cells from human pluripotent stem cells (hPSCs).

The invention provides methods of isolating human cardiomyogenic progenitor cells, in particular cells that are biased to the ventricular lineage, as well as isolated clonal populations of such progenitor cells, based on the discovery that LIFR and FGFR3 are cell surface markers for cardiac ventricular progenitor cells. In vitro and in vivo uses for these cardiac ventricular progenitor cells are also provided.

In order that the present invention may be more readily understood, certain terms are first defined. Additional definitions are set forth throughout the detailed description.

As used herein, the terms "Leukemia Inhibitor Factor Receptor", "LIF Receptor" and "LIFR" are used interchangeably to refer to a protein known in the art that has been described in, for example, Gearing, D. et al. (1991) *EMBO J.* 10:2839-2848; Gearing, D. and Bruce, A. G. (1992) *New. Biol.* 4:61-65; and Schiemann, W. P. et al. (1995) *Proc. Natl. Acad. Sci. USA* 92:5361-5365. LIFR is also referred to in the art as Leukemia Inhibitor Factor Receptor Alpha, CD118, CD118 antigen, SJ52, STWS and SWS. A non-limiting example of a LILFR protein is the human protein having the amino acid sequence set forth in Genbank Accession Number NP_001121143.1.

As used herein, the terms "Fibroblast Growth Factor Receptor 3", "FGF Receptor 3" and "FGFR3" are used interchangeably to refer to a protein known in the art that has been described in, for example, Keegan, K. et al. (1991) *Proc. Natl. Acad. Sci. USA* 88:1095-1099; Thompson, L. M. et al. (1991) *Genomics* 11:1133-1142; and Shiang, R. et al. (1994) *Cell* 78:335-343. FGFR3 is also referred to in the art as CD333, CD333 antigen, EC 2.7.10.1, JTK4, ACH, CEK2 and HSFGFR3EX. A non-limiting example of an FGFR3 protein is the human protein having the amino acid sequence set forth in Genbank Accession Number NP_000133.1.

As used herein, the term "stem cells" is used in a broad sense and includes traditional stem cells, progenitor cells, pre-progenitor cells, reserve cells, and the like. The term "stem cell" or "progenitor" are used interchangeably herein, and refer to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation".

The term "progenitor cell" is used herein to refer to cells that have a cellular phenotype that is more primitive (e.g., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "pluripotent" as used herein refers to a cell with the capacity, under different conditions, to differentiate to cell types characteristic of all three germ cell layers (endoderm, mesoderm and ectoderm). Pluripotent cells are characterized primarily by their ability to differentiate to all three germ layers, using, for example, a nude mouse and teratomas formation assay. Pluripotency is also evidenced by the expression of embryonic stem (ES) cell markers, although the preferred test for pluripotency is the demonstration of the capacity to differentiate into cells of each of the three germ layers. In some embodiments, a pluripotent cell is an undifferentiated cell.

The term "pluripotency" or a "pluripotent state" as used herein refers to a cell with the ability to differentiate into all three embryonic germ layers: endoderm (gut tissue), mesoderm (including blood, muscle, and vessels), and ectoderm (such as skin and nerve), and typically has the potential to divide in vitro for a long period of time, e.g., greater than one year or more than 30 passages.

The term "multipotent" when used in reference to a "multipotent cell" refers to a cell that is able to differentiate into some but not all of the cells derived from all three germ layers. Thus, a multipotent cell is a partially differentiated cell. Multipotent cells are well known in the art, and examples of multipotent cells include adult stem cells, such as for example, hematopoietic stem cells and neural stem cells. Multipotent means a stem cell may form many types of cells in a given lineage, but not cells of other lineages. For example, a multipotent blood stem cell can form the many different types of blood cells (red, white, platelets, etc.), but it cannot form neurons.

The term "embryonic stem cell" or "ES cell" or "ESC" are used interchangeably herein and refer to the pluripotent stem cells of the inner cell mass of the embryonic blastocyst (see U.S. Pat. Nos. 5,843,780, 6,200,806, which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like. In some embodiments, an ES cell can be obtained without destroying the embryo, for example, without destroying a human embryo.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture.

Exemplary adult stem cells include neural stem cells, neural crest stem cells, mesenchymal stem cells, hematopoietic stem cells, and pancreatic stem cells. As indicated above, stem cells have been found resident in virtually every tissue. Accordingly, the present invention appreciates that stem cell populations can be isolated from virtually any animal tissue.

The term "human pluripotent stem cell" (abbreviated as hPSC), as used herein, refers to a human cell that has the capacity to differentiate into a variety of different cell types as discussed above regarding stem cells and pluripotency. Human pluripotent human stem cells include, for example, induced pluripotent stem cells (iPSC) and human embryonic stem cells, such as ES cell lines.

The term "human cardiac progenitor cell", as used herein, refers to a human progenitor cell that is committed to the cardiac lineage and that has the capacity to differentiate into all three cardiac lineage cells (cardiac muscle cells, endothelial cells and smooth muscle cells).

The term "human cardiomyogenic progenitor cell", as used herein, refers to a human progenitor cell that is committed to the cardiac lineage and that predominantly differentiates into cardiac muscle cells (i.e., more than 50% of the differentiated cells, preferably more than 60%, 70%, 80% or 90% of the differentiated cells, derived from the progenitor cells are cardiac muscle cells).

The term "cardiac ventricular progenitor cell", as used herein, refers to a progenitor cell that is committed to the cardiac lineage and that predominantly differentiates into cardiac ventricular muscle cells (i.e., more than 50% of the differentiated cells, preferably more than 60%, 70%, 80% or 90% of the differentiated cells, derived from the progenitor cells are cardiac ventricular muscle cells). This type of cell is also referred to herein as a human ventricular progenitor, or HVP, cell.

The term "cardiomyocyte" refers to a muscle cell of the heart (e.g. a cardiac muscle cell). A cardiomyocyte will generally express on its cell surface and/or in the cytoplasm one or more cardiac-specific marker. Suitable cardiomyocyte-specific markers include, but are not limited to, cardiac troponin I, cardiac troponin-C, tropomyosin, caveolin-3, GATA-4, myosin heavy chain, myosin light chain-2a, myosin light chain-2v, ryanodine receptor, and atrial natriuretic factor. The term "derived from" used in the context of a cell derived from another cell means that a cell has stemmed (e.g. changed from or produced by) a cell that is a different cell type. The term "derived from" also refers to cells that have been differentiated from a progenitor cell.

The term "Isl1+ cardiac progenitor cell", as used herein, refers to a human progenitor cell that is committed to the cardiac lineage and that expresses Islet 1.

The term "Isl1+ LIFR+ cardiac progenitor cell", as used herein, refers to a human progenitor cell that is committed to the cardiac lineage and that expresses both Islet 1 and LIFR.

The term "Isl1+ FGFR3+ cardiac progenitor cell", as used herein, refers to a human progenitor cell that is committed to the cardiac lineage and that expresses both Islet 1 and FGFR3.

The term "Isl1+ LIFR+ FGFR3+ cardiac progenitor cell", as used herein, refers to a human progenitor cell that is committed to the cardiac lineage and that expresses Islet 1, LIFR and FGFR3.

With respect to cells in cell cultures or in cell populations, the term "substantially free of" means that the specified cell type of which the cell culture or cell population is free, is present in an amount of less than about 10%, less than about 9%, less than about 8%, less than about 7%, less than about 6%, less than about 5%, less than about 4%, less than about 3%, less than about 2% or less than about 1% of the total number of cells present in the cell culture or cell population.

In the context of cell ontogeny, the adjective "differentiated", or "differentiating" is a relative term. A "differentiated cell" is a cell that has progressed further down the developmental pathway than the cell it is being compared with. Thus, stem cells can differentiate to lineage-restricted precursor cells (such as a mesodermal stem cell), which in turn can differentiate into other types of precursor cells further down the pathway (such as an cardiomyocyte precursor), and then to an end-stage differentiated cell, which plays a characteristic role in a certain tissue type, and may or may not retain the capacity to proliferate further.

The term "differentiation" in the present context means the formation of cells expressing markers known to be associated with cells that are more specialized and closer to becoming terminally differentiated cells incapable of further differentiation. The pathway along which cells progress from a less committed cell, to a cell that is increasingly committed to a particular cell type, and eventually to a terminally differentiated cell is referred to as progressive differentiation or progressive commitment. Cell which are more specialized (e.g., have begun to progress along a path of progressive differentiation) but not yet terminally differentiated are referred to as partially differentiated. Differentiation is a developmental process whereby cells assume a specialized phenotype, e.g., acquire one or more characteristics or functions distinct from other cell types. In some cases, the differentiated phenotype refers to a cell phenotype that is at the mature endpoint in some developmental pathway (a so called terminally differentiated cell). In many, but not all tissues, the process of differentiation is coupled with exit from the cell cycle. In these cases, the terminally differentiated cells lose or greatly restrict their capacity to proliferate. However, we note that in the context of this specification, the terms "differentiation" or "differentiated" refer to cells that are more specialized in their fate or function than at a previous point in their development, and includes both cells that are terminally differentiated and cells that, although not terminally differentiated, are more specialized than at a previous point in their development. The development of a cell from an uncommitted cell (for example, a stem cell), to a cell with an increasing degree of commitment to a particular differentiated cell type, and finally to a terminally differentiated cell is known as progressive differentiation or progressive commitment. A cell that is "differentiated" relative to a progenitor cell has one or more phenotypic differences relative to that progenitor cell. Phenotypic differences include, but are not limited to morphologic differences and differences in gene expression and biological activity, including not only the presence or absence of an expressed marker, but also differences in the amount of a marker and differences in the co-expression patterns of a set of markers.

The term "differentiation" as used herein refers to the cellular development of a cell from a primitive stage towards a more mature (i.e. less primitive) cell.

As used herein, "proliferating" and "proliferation" refers to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The terms "renewal" or "self-renewal" or "proliferation" are used interchangeably herein, and refers to a process of a cell making more copies of itself (e.g. duplication) of the cell. In some embodiments, cells are capable of renewal of themselves by dividing into the same undifferentiated cells (e.g. progenitor cell type) over long periods, and/or many months to years. In some instances, proliferation refers to the expansion of cells by the repeated division of single cells into two identical daughter cells.

The term "lineages" as used herein refers to a term to describe cells with a common ancestry or cells with a common developmental fate, for example cells that have a developmental fate to develop into ventricular cardiomyocytes.

The term "clonal population", as used herein, refers to a population of cells that is derived from the outgrowth of a single cell. That is, the cells within the clonal population are all progeny of a single cell that was used to seed the clonal population.

The term "media" as referred to herein is a medium for maintaining a tissue or cell population, or culturing a cell population (e.g. "culture media") containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The term "phenotype" refers to one or a number of total biological characteristics that define the cell or organism under a particular set of environmental conditions and factors, regardless of the actual genotype.

A "marker" as used herein describes the characteristics and/or phenotype of a cell. Markers can be used for selection of cells comprising characteristics of interest. Markers will vary with specific cells. Markers are characteristics, whether morphological, functional or biochemical (enzymatic) characteristics particular to a cell type, or molecules expressed by the cell type. Preferably, such markers are proteins, and more preferably, possess an epitope for antibodies or other binding molecules available in the art. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers may be detected by any method available to one of skill in the art.

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from.

The term "substantially pure", with respect to a particular cell population, refers to a population of cells that is at least about 75%, preferably at least about 85%, more preferably at least about 90%, and most preferably at least about 95% pure, with respect to the cells making up a total cell population.

The terms "subject" and "individual" are used interchangeably herein, and refer to an animal, for example a human, to whom cardiac ventricular progenitor cells as disclosed herein can be implanted into, for e.g. treatment, which in some embodiments encompasses prophylactic treatment or for a disease model, with methods and compositions described herein, is or are provided. For treatment of disease states that are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like are also encompassed in the term subject.

As used herein, the term "recipient" refers to a subject that will receive a transplanted organ, tissue or cell.

The term "three-dimensional matrix" or "scaffold" or "matrices" as used herein refers in the broad sense to a composition comprising a biocompatible matrix, scaffold, or the like. The three-dimensional matrix may be liquid, gel, semi-solid, or solid at 25° C. The three-dimensional matrix may be biodegradable or non-biodegradable. In some embodiments, the three-dimensional matrix is biocompatible, or bioresorbable or bioreplacable. Exemplary three-dimensional matrices include polymers and hydrogels comprising collagen, fibrin, chitosan, MATRIGEL™, polyethylene glycol, dextrans including chemically crosslinkable or photocrosslinkable dextrans, processed tissue matrix such as submucosal tissue and the like. In certain embodiments, the three-dimensional matrix comprises allogeneic components, autologous components, or both allogeneic components and autologous components. In certain embodiments, the three-dimensional matrix comprises synthetic or semi-synthetic materials. In certain embodiments, the three-dimensional matrix comprises a framework or support, such as a fibrin-derived scaffold.

As used herein, the terms "administering," "introducing" and "transplanting" are used interchangeably and refer to the placement of cardiomyogenic progenitor cells and/or cardiomyocytes differentiated as described herein into a subject by a method or route which results in at least partial localization of the cells at a desired site. The cells can be administered by any appropriate route that results in delivery to a desired location in the subject where at least a portion of the cells remain viable. The period of viability of the cells after administration to a subject can be as short as a few hours, e.g. twenty-four hours, to a few days, to as long as several years.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value. The term "substantially" or "predominantly" as used herein means a proportion of at least about 60%, or preferably at least about 70% or at least about 80%, or at least about 90%, at least about 95%, at least about 97% or at least about 99% or more, or any integer between 70% and 100%.

The term "disease" or "disorder" is used interchangeably herein, and refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, indisposition or affection.

As used herein, the phrase "cardiovascular condition, disease or disorder" is intended to include all disorders characterized by insufficient, undesired or abnormal cardiac function, e.g. ischemic heart disease, hypertensive heart disease and pulmonary hypertensive heart disease, valvular disease, congenital heart disease and any condition which leads to congestive heart failure in a subject, particularly a human subject. Insufficient or abnormal cardiac function can be the result of disease, injury and/or aging. By way of background, a response to myocardial injury follows a well-defined path in which some cells die while others enter a state of hibernation where they are not yet dead but are dysfunctional. This is followed by infiltration of inflammatory cells, deposition of collagen as part of scarring, all of which happen in parallel with in-growth of new blood vessels and a degree of continued cell death. As used herein, the term "ischemia" refers to any localized tissue ischemia due to reduction of the inflow of blood. The term "myocardial ischemia" refers to circulatory disturbances caused by coronary atherosclerosis and/or inadequate oxygen supply to the myocardium. For example, an acute myocardial infarction represents an irreversible ischemic insult to myocardial tissue. This insult results in an occlusive (e.g., thrombotic or embolic) event in the coronary circulation and produces an environment in which the myocardial metabolic demands exceed the supply of oxygen to the myocardial tissue.

As used herein, the term "treating" or "treatment" are used interchangeably herein and refers to reducing or decreasing or alleviating or halting at least one adverse effect or symptom of a cardiovascular condition, disease or disorder, i.e., any disorder characterized by insufficient or undesired cardiac function. Adverse effects or symptoms of cardiac disorders are well-known in the art and include, but are not limited to, dyspnea, chest pain, palpitations, dizziness, syncope, edema, cyanosis, pallor, fatigue and death. In some embodiments, the term "treatment" as used herein refers to prophylactic treatment or preventative treatment to prevent the development of a symptom of a cardiovascular condition in a subject.

Treatment is generally "effective" if one or more symptoms or clinical markers are reduced as that term is defined herein. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with a cardiac condition, as well as those likely to develop a cardiac condition due to genetic susceptibility or other factors such as weight, diet and health. In some embodiments, the term to treat also encompasses preventative measures and/or prophylactic treatment, which includes administering a pharmaceutical composition as disclosed herein to prevent the onset of a disease or disorder.

A therapeutically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It will be understood, that the total daily usage of the compositions and formulations as disclosed herein will be decided by the attending physician within the scope of sound medical judgment. The exact amount required will vary depending on factors such as the type of disease being treated.

With reference to the treatment of a cardiovascular condition or disease in a subject, the term "therapeutically effective amount" refers to the amount that is safe and sufficient to prevent or delay the development or a cardiovascular disease or disorder. The amount can thus cure or cause the cardiovascular disease or disorder to go into remission, slow the course of cardiovascular disease progression, slow or inhibit a symptom of a cardiovascular disease or disorder, slow or inhibit the establishment of secondary symptoms of a cardiovascular disease or disorder or inhibit the development of a secondary symptom of a cardiovascular disease or disorder. The effective amount for the treatment of the cardiovascular disease or disorder depends on the type of cardiovascular disease to be treated, the severity of the symptoms, the subject being treated, the age and general condition of the subject, the mode of administration and so forth. Thus, it is not possible to specify the exact "effective amount". However, for any given case, an appropriate "effective amount" can be determined by one of ordinary skill in the art using only routine experimentation. The efficacy of treatment can be judged by an ordinarily skilled practitioner, for example, efficacy can be assessed in animal models of a cardiovascular disease or disorder as discussed herein, for example treatment of a rodent with acute myocardial infarction or ischemia-reperfusion injury, and any treatment or administration of the compositions or formulations that leads to a decrease of at least one symptom of the cardiovascular disease or disorder as disclosed herein, for example, increased heart ejection fraction, decreased rate of heart failure, decreased infarct size, decreased associated morbidity (pulmonary edema, renal failure, arrhythmias) improved exercise tolerance or other quality of life measures, and decreased mortality indicates effective treatment. In embodiments where the compositions are used for the treatment of a cardiovascular disease or disorder, the efficacy of the composition can be judged using an experimental animal model of cardiovascular disease, e.g., animal models of ischemia-reperfusion injury (Headrick J P, Am J Physiol Heart circ Physiol 285; H1797; 2003) and animal models acute myocardial infarction. (Yang Z, Am J Physiol Heart Circ. Physiol 282:H949:2002; Guo Y, J Mol Cell Cardiol 33; 825-830, 2001). When using an experimental animal model, efficacy of treatment is evidenced when a reduction in a symptom of the cardiovascular disease or disorder, for example, a reduction in one or more symptom of dyspnea, chest pain, palpitations, dizziness, syncope, edema, cyanosis, pallor, fatigue and high blood pressure which occurs earlier in treated, versus untreated animals. By "earlier" is meant that a decrease, for example in the size of the tumor occurs at least 5% earlier, but preferably more, e.g., one day earlier, two days earlier, 3 days earlier, or more.

As used herein, the term "treating" when used in reference to a treatment of a cardiovascular disease or disorder is used to refer to the reduction of a symptom and/or a biochemical marker of a cardiovascular disease or disorder, for example a reduction in at least one biochemical marker of a cardiovascular disease by at least about 10% would be considered an effective treatment. Examples of such biochemical markers of cardiovascular disease include a reduction of, for example, creatine phosphokinase (CPK), aspartate aminotransferase (AST), lactate dehydrogenase (LDH) in the blood, and/or a decrease in a symptom of cardiovascular disease and/or an improvement in blood flow and cardiac function as determined by someone of ordinary skill in the art as measured by electrocardiogram (ECG or EKG), or echocardiogram (heart ultrasound), Doppler ultrasound and nuclear medicine imaging. A reduction in a symptom of a cardiovascular disease by at least about 10% would also be considered effective treatment by the methods as disclosed herein. As alternative examples, a reduction in a symptom of cardiovascular disease, for example a reduction of at least one of the following; dyspnea, chest pain, palpitations, dizziness, syncope, edema, cyanosis etc. by at least about 10% or a cessation of such systems, or a reduction in the size one such symptom of a cardiovascular disease by at least about 10% would also be considered as affective treatments by the methods as disclosed herein. In some embodiments, it is preferred, but not required that the therapeutic agent actually eliminate the cardiovascular disease or disorder, rather just reduce a symptom to a manageable extent.

Subjects amenable to treatment by the methods as disclosed herein can be identified by any method to diagnose myocardial infarction (commonly referred to as a heart attack) commonly known by persons of ordinary skill in the art are amenable to treatment using the methods as disclosed herein, and such diagnostic methods include, for example but are not limited to; (i) blood tests to detect levels of creatine phosphokinase (CPK), aspartate aminotransferase (AST), lactate dehydrogenase (LDH) and other enzymes released during myocardial infarction; (ii) electrocardiogram (ECG or EKG) which is a graphic recordation of cardiac activity, either on paper or a computer monitor. An ECG can be beneficial in detecting disease and/or damage; (iii) echocardiogram (heart ultrasound) used to investigate congenital heart disease and assessing abnormalities of the heart wall, including functional abnormalities of the heart wall, valves and blood vessels; (iv) Doppler ultrasound can be used to measure blood flow across a heart valve; (v) nuclear medicine imaging (also referred to as radionuclide scanning in the art) allows visualization of the anatomy and function of an organ, and can be used to detect coronary artery disease, myocardial infarction, valve disease, heart transplant rejection, check the effectiveness of bypass surgery, or to select patients for angioplasty or coronary bypass graft.

The terms "coronary artery disease" and "acute coronary syndrome" as used interchangeably herein, and refer to myocardial infarction refer to a cardiovascular condition, disease or disorder, include all disorders characterized by insufficient, undesired or abnormal cardiac function, e.g. ischemic heart disease, hypertensive heart disease and pulmonary hypertensive heart disease, valvular disease, congenital heart disease and any condition which leads to congestive heart failure in a subject, particularly a human subject. Insufficient or abnormal cardiac function can be the result of disease, injury and/or aging. By way of background, a response to myocardial injury follows a well-defined path in which some cells die while others enter a state of hibernation where they are not yet dead but are dysfunctional. This is followed by infiltration of inflammatory cells, deposition of collagen as part of scarring, all of which happen in parallel with in-growth of new blood vessels and a degree of continued cell death.

As used herein, the term "ischemia" refers to any localized tissue ischemia due to reduction of the inflow of blood. The term "myocardial ischemia" refers to circulatory disturbances caused by coronary atherosclerosis and/or inadequate oxygen supply to the myocardium. For example, an acute myocardial infarction represents an irreversible ischemic insult to myocardial tissue. This insult results in an occlusive (e.g., thrombotic or embolic) event in the coronary circulation and produces an environment in which the myocardial metabolic demands exceed the supply of oxygen to the myocardial tissue.

The terms "composition" or "pharmaceutical composition" used interchangeably herein refer to compositions or formulations that usually comprise an excipient, such as a pharmaceutically acceptable carrier that is conventional in the art and that is suitable for administration to mammals, and preferably humans or human cells. In some embodiments, pharmaceutical compositions can be specifically formulated for direct delivery to a target tissue or organ, for example, by direct injection or via catheter injection to a target tissue. In other embodiments, compositions can be specifically formulated for administration via one or more of a number of routes, including but not limited to, oral, ocular parenteral, intravenous, intraarterial, subcutaneous, intranasal, sublingual, intraspinal, intracerebroventricular, and the like. In addition, compositions for topical (e.g., oral mucosa, respiratory mucosa) and/or oral administration can form solutions, suspensions, tablets, pills, capsules, sustained-release formulations, oral rinses, or powders, as known in the art are described herein. The compositions also can include stabilizers and preservatives. For examples of carriers, stabilizers and adjuvants, University of the Sciences in Philadelphia (2005) Remington: The Science and Practice of Pharmacy with Facts and Comparisons, 21st Ed.

As used herein, the terms "administering," "introducing" and "transplanting" are used interchangeably and refer to the placement of a pharmaceutical composition comprising cardiomyogenic progenitor cells, or a composition comprising a population of differentiated cardiomyocytes (e.g., ventricular cardiomyocytes) as described herein, into a subject by a method or route which results in at least partial localization of the pharmaceutical composition, at a desired site or tissue location. In some embodiments, the pharmaceutical composition can be administered by any appropriate route which results in effective treatment in the subject, i.e. administration results in delivery to a desired location or tissue in the subject where at least a portion of the cells are located at a desired target tissue or target cell location.

The phrases "parenteral administration" and "administered parenterally" as used herein mean modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein mean the administration of cardiovascular stem cells and/or their progeny and/or compound and/or other material other than directly into the cardiac tissue, such that it enters the animal's system and, thus, is subject to metabolism and other like processes, for example, subcutaneous or intravenous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation.

The term "drug" or "compound" or "test compound" as used herein refers to a chemical entity or biological product, or combination of chemical entities or biological products, administered to a subject to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The term "transplantation" as used herein refers to introduction of new cells (e.g. reprogrammed cells), tissues (such as differentiated cells produced from reprogrammed cells), or organs into a host (i.e. transplant recipient or transplant subject)

The term "agent reactive with LIFR", as used herein, refers to an agent that binds to or otherwise interacts with LIFR. Preferably, the agent "specifically" binds or otherwise interacts with LIFR such that it does not bind or interact with other non-LIFR proteins.

The term "agent reactive with FGFR3", as used herein, refers to an agent that binds to or otherwise interacts with FGFR3. Preferably, the agent "specifically" binds or otherwise interacts with FGFR3 such that it does not bind or interact with other non-FGFR3 proteins.

The term "agent reactive with Islet 1", as used herein, refers to an agent that binds to or otherwise interacts with Islet 1. Preferably, the agent "specifically" binds or otherwise interacts with Islet 1 such that it does not bind or interact with other non-Islet 1 proteins.

The term "antibody", as used herein, includes whole antibodies and any antigen binding fragment (i.e., "antigen-binding portion") or single chain thereof. An "antibody" refers, in one preferred embodiment, to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The term "antigen-binding portion" of an antibody (or simply "antibody portion"), as used herein, refers to one or more fragments of an antibody that retain the ability to specifically bind to an antigen.

The term "monoclonal antibody," as used herein, refers to an antibody that displays a single binding specificity and affinity for a particular epitope.

The term "human monoclonal antibody", as used herein, refers to an antibody which displays a single binding specificity and which has variable and optional constant regions derived from human germline immunoglobulin sequences.

The term "humanized monoclonal antibody", as used herein, refers to an antibody which displays a single binding specificity and which has heavy and light chain CDR1, 2 and 3 from a non-human antibody (e.g., a mouse monoclonal antibody) grafted into human framework and constant regions.

The term "chimeric monoclonal antibody", as used herein, refers to an antibody which displays a single binding specificity and which has heavy and light chain variable regions from one species linked to constant regions from another species.

The term "fusion protein", as used herein, refers to a composite protein, typically made using recombinant DNA technology, in which two different proteins, or portions thereof, are operatively linked together. A non-limiting example is an Fc fusion protein in which a non-immunoglobulin protein is operatively linked to an immunoglobulin Fc region.

Various aspects of the invention are described in further detail in the following subsections.

Methods of Isolating Human Cardiac Ventricular Progenitor Cells

In one aspect, the invention pertains to methods of isolating human cardiac ventricular progenitor cells. As described in the Examples, LIFR and FGFR3 have now been identified as a cell surface marker of human cardiac ventricular progenitor cells and thus these markers can be used to facilitate isolation of these progenitor cells. Accordingly, in one embodiment, the invention provides a method for isolating human cardiac ventricular progenitor cells, the method comprising:

contacting a culture of human cells containing cardiac progenitor cells with one or more agents reactive with LIFR and/or FGFR3; and separating LIFR and/or FGFR3 reactive positive cells from non-reactive cells to thereby isolate human cardiac ventricular progenitor cells.

Alternatively, after the contacting step, the method can comprise isolating LIFR and/or FGFR3 reactive positive cells from non-reactive cells to thereby isolate human cardiac ventricular progenitor cells.

Also as described in the Examples, Islet 1 is a marker that is co-expressed with LIFR and/or FGFR3 by the cardiac ventricular progenitor cells and thus both markers can be used to facilitate isolation of these progenitor cells. Accordingly, in another embodiment of the above method, the culture of human cells is also contacted with an agent reactive with Islet 1; and LIFR reactive/Islet 1 reactive positive cells, FGFR3 reactive/Islet 1 reactive positive cells or LIFR reactive/FGFR3 reactive/Islet 1 reactive positive cells are separated from non-reactive cells to thereby isolate human cardiac ventricular progenitor cells. The culture of human cells can be simultaneously contacted with the agent(s) reactive with LIFR and/or FGFR3 and the agent reactive with Islet 1. Alternatively, the culture of human cells can be contacted with the agent reactive with Islet 1 before contacting with the agent(s) reactive with LIFR and/or FGFR3. Alternatively, the culture of human cells can be contacted with the agent(s) reactive with LIFR and/or FGFR3 before contacting with the agent reactive with Islet 1.

In yet another embodiment, the culture of human cells can be contacted with an agent reactive with LIFR and an agent reactive with FGFR3, and cells that are LIFR+/FGFR3+ can be separated. In yet another embodiment, the culture of human cells can be contacted with an agent reactive with LIFR, an agent reactive with FGFR3 and an agent reactive with Islet 1, and cells that are LIFR+/FGFR3+/Islet 1+ can be separated.

In another embodiment, the invention provides a method for isolating human cardiac ventricular progenitor cells, the method comprising:

culturing human pluripotent stem cells under conditions that generate cardiac progenitor cells to obtain a culture of cells;

contacting the culture of cells with one or more agents reactive with LIFR and/or FGFR3; and separating LIFR reactive positive cells and/or FGFR3 reactive positive cells from non-reactive cells to thereby isolate human cardiac ventricular progenitor cells.

Alternatively, after the culturing and contacting steps, the method can comprise isolating LIFR and/or FGFR3 reactive positive cells from non-reactive cells to thereby isolate human cardiac ventricular progenitor cells.

In one embodiment of the above method, the culture of human cells is also contacted with an agent reactive with Islet 1; and LIFR reactive/Islet 1 reactive, FGFR3 reactive/Islet 1 reactive positive cells or LIFR reactive/FGFR3 reactive/Islet 1 reactive positive cells are separated from non-reactive cells to thereby isolate human cardiac ventricular progenitor cells. The culture of human cells can be simultaneously contacted with the agent(s) reactive with LIFR and/or FGFR3 and the agent(s) reactive with Islet 1. Alternatively, the culture of human cells can be contacted with the agent(s) reactive with Islet 1 before contacting with the agent reactive with LIFR and/or FGFR3. Alternatively, the culture of human cells can be contacted with the agent(s) reactive with LIFR and/or FGFR3 before contacting with the agent reactive with Islet 1.

In yet another embodiment, the culture of human cells can be contacted with an agent reactive with LIFR and an agent reactive with FGFR3, and cells that are LIFR+/FGFR3+ can be separated. In yet another embodiment, the culture of human cells can be contacted with an agent reactive with LIFR, an agent reactive with FGFR3 and an agent reactive with Islet 1, and cells that are LIFR+/FGFR3+/Islet 1+ can be separated.

In a preferred embodiment, the agent reactive with LIFR is an anti-LIFR antibody, such as a monoclonal antibody. Non-limiting examples include murine, rabbit, human, humanized or chimeric monoclonal antibodies with binding specificity for LIFR. Anti-LIFR monoclonal antibodies are commercially available in the art (e.g., R&D Systems, Santa Cruz Biotechnology). Moreover, anti-LIFR antibodies can be prepared using standard techniques well established in the art using LIFR as the antigen.

In another embodiment, the agent reactive with LIFR is a LIFR ligand, such as a soluble LIFR ligand or a soluble LIFR ligand fusion protein. Non-limiting examples of LIFR ligands include leukemia inhibitory factor (LIF), oncostatin M (OSM) and cardiotrophin-1 (CT-1). Preferably, the LIFR ligand is LIF. Soluble LIFR ligands can be prepared using standard recombinant DNA techniques, for example by deletion of the transmembrane and cytoplasmic domains. A soluble ligand can be transformed into a soluble ligand fusion protein also using standard recombinant DNA techniques. A fusion protein can be prepared in which fusion partner can comprise a binding moiety that facilitates separation of the fusion protein.

Similarly, the agent reactive with FGFR3 can be, for example, an anti-FGFR3 antibody (e.g., monoclonal antibody) or a FGFR3 ligand, such as a FGFR3 ligand fusion protein. Non-limiting examples include murine, rabbit, human, humanized or chimeric monoclonal antibodies with binding specificity for FGFR3. Anti-FGFR3 monoclonal antibodies are commercially available in the art (e.g., R&D Systems, Santa Cruz Biotechnology). Moreover, anti-FGFR3 antibodies can be prepared using standard techniques well established in the art using FGFR3 as the antigen. Non-limiting examples of FGFR3 ligands include Fibroblast Growth Factor 1 (FGF1), Fibroblast Growth Factor 2 (FGF2) and Fibroblast Growth Factor 9 (FGF9).

Similarly, the agent reactive with Islet 1 can be, for example, an anti-Islet 1 antibody (e.g., monoclonal antibody) or an Islet 1 ligand, such as an Islet 1 ligand fusion protein.

In order to separate the LIFR and/or FGFR3 reactive positive cells from non-reactive cells, one of a variety of different cell separation techniques known in the art can be used. Preferably, the LIFR and/or FGFR3 reactive positive cells are separated from non-reactive cells by fluorescence activated cell sorting (FACS). The FACS technology, and apparatuses for carrying it out to separate cells, is well established in the art. When FACS is used for cell separation, preferably the agent(s) reactive with LIFR and/or FGFR3 that is used is a fluorescently-labeled anti-LIFR and/or anti-FGFR3 monoclonal antibody. Alternatively, cell separation can be achieved by, for example, magnetic activated cell sorting (MACS). When MACS is used for cell separation, preferably the agent reactive with LIFR or FGFR3 that is used is magnetic nanoparticles coated with anti-LIFR or anti-FGFR3 monoclonal antibody. Alternatively, other single cell sorting methodologies known in the art can be applied to the methods of isolating cardiac ventricular progenitor cells of the invention, including but not limited to IsoRaft array and DEPArray technologies.

Prior to contact with the agent(s) reactive with LIFR and/or FGFR3, and separation of LIFR and/or FGFR3 reactive cells, human pluripotent stem cells can be cultured under conditions that lead to the generation of cardiac progenitor cells. Culture conditions for generating cardiac progenitor cells have been described in the art (see e.g., Lian, X. et al. (2012) *Proc. Natl. Acad. Sci. USA* 109:E1848-1857; U.S. Patent Publication No. 20130189785) and also are described in detail in Example 1 and FIG. 1, as well as in Example 10. Typically, Wnt/β-catenin signaling is first activated in the hPSCs, followed by an incubation period, followed by inhibition of Wnt/β-catenin signaling. Activation of Wnt/β-catenin signaling is achieved by incubation with a Gsk3 inhibitor, preferably CHIR98014 (CAS 556813-39-9). Inhibition of Wnt/β-catenin signaling is achieved by incubation with a Porcn inhibitor, preferably Wnt-059 (CAS 1243243-89-1). Suitable hPSCs for use in the methods of the invention include induced pluripotent stem cells (iPSC), such as 19-11-1, 19-9-7 or 6-9-9 cells (Yu, J. et al. (2009) *Science* 324:797-801), and human embryonic stem cell lines, such as ES03 cells (WiCell Research Institute) or H9 cells (Thomson, J. A. et al. (1998) *Science* 282:1145-1147). Suitable culture media for generating cardiomyogenic progenitors include E8 medium, mTeSR1 medium and RPMI/B27 minus insulin, each described further in Example 1 and/or Example 10.

Preferably, the human cardiomyogenic progenitor cells are ventricular progenitor cells. Culture conditions have now been determined that bias the cardiomyogenic progenitor cells to the ventricular lineage. These ventricular cardiomyogenic progenitor cells can be cultured in RPMI/B27 medium and they can further differentiate into ventricular muscle cells. A preferred medium for culturing the cardiac ventricular progenitor cells in vitro such that they differentiation into ventricular cells in vitro (e.g., expressing the MLC2v marker described below) is the Cardiac Progenitor Culture (CPC) medium (advanced DMEM/F12 supplemented with 20% KnockOut Serum Replacement, 2.5 mM GlutaMAX and 100 µg/ml Vitamin C).

Known markers of differentiated cardiac cells can be used to identify the type(s) of cells that are generated by differentiation of the cardiac progenitor cells. For example, cardiac troponin I (cTnI) can be used as a marker of cardiomyocyte differentiation. CD144 (VE-cadherin) can be used as a marker of endothelial cells. Smooth muscle actin (SMA) can be used as a marker of smooth muscle cells. MLC2v can be used as a marker of ventricular muscle cells. MLC2a, which is expressed on both immature ventricular muscle cells and atrial muscle cells, can be used as a marker for those cell types. Additionally, sarcolipin, which is specifically expressed in atrial muscle cells, can be used as a marker for atrial muscle cells. Phospholamban, which is expressed predominantly in the ventricles and, to a lesser extent, in the atria, can also be used as a marker. Hairy-related transcription factor 1 (HRT1), also called Hey1, which is expressed in atrial cardiomyocytes, can be used as a marker for atrial cardiomyocytes. HRT2 (Hey2), which is expressed in ventricular cardiomyocytes, can be used as a marker for ventricular cardiomyocytes. In addition, IRX4 has a ventricular-restricted expression pattern during all stages of development, and thus can be used as a ventricular lineage marker. In summary, the genes expressed in the ventricles, and thus which are appropriate ventricular markers, are: MLC2v, IRX4 and HRT2, while genes expressed in the atria, and thus which are appropriate atrial markers are: MLC2a, HRT1, Sarcolipin and ANF (atrial natriuretic factor). The preferred marker of ventricular differentiation is MLC2v.

Clonal Populations of Human Cardiac Ventricular Progenitor Cells

In another aspect, the invention provides methods for obtaining a clonal population of human cardiac ventricular progenitor cells, as well as isolated clonal populations of such progenitors. The invention allows for the expansion and propagation of the cardiac ventricular progenitor cells such that a clonal population of a billion or more cells can be achieved. The ability to clonally expand the LIFR+ and/or FGFR3+ cardiac ventricular progenitor cells to such large numbers is a necessary feature for successful use of these cells in vivo to enhance cardiac function, since such a use requires on the order of a billion or more cells.

Accordingly, in another aspect, the invention provides a method for obtaining a clonal population of human cardiac ventricular progenitor cells, the method comprising:

isolating a single LIFR+ and/or FGFR3+ human cardiac ventricular progenitor cell; and culturing the single LIFR+ and/or FGFR3+ human cardiac ventricular progenitor cell under conditions such that the cell is expanded to at least $1 \times 10^9$ cells to thereby obtain a clonal population of human cardiac ventricular progenitor cells.

In a preferred embodiment, the single LIFR+ and/or FGFR3+ human cardiac ventricular progenitor cell is Islet 1 positive, Nkx2.5 negative and flk1 negative at the time of initial culture. As described further in the Examples, such a single cell can be obtained at approximately day 6 of the culture under conditions that promote the generation of cardiomyogenic progenitors. The clonal population of human cardiac ventricular progenitors can be further cultured and differentiated in vitro such that the cells express the ventricular maker MLC2v.

Preferably, the single LIFR+ and/or FGFR3+ human cardiac ventricular progenitor cell is isolated by fluorescence activated cell sorting. Alternatively, the cell can be isolated by MACS or by other cell sorting methods known in the art and/or described herein.

Preferably, the single LIFR+ and/or FGFR3+ human cardiac ventricular progenitor cell is isolated using one or more agents reactive with LIFR and/or FGFR3, such as an anti-LIFR antibody or other agent reactive with LIFR as described hereinbefore, or an anti-FGFR3 antibody or other agent reactive with FGFR3 as described hereinbefore.

In other embodiments, the clonal population of human cardiac ventricular progenitor cells is LIFR+ and FGFR3+. Such double-positive cells can be isolated and clonally expanded as described herein before using both an agent reactive with LIFR and an agent reactive with FGFR3.

In a preferred embodiment, the single LIFR+ and/or FGFR3+ human cardiac ventricular progenitor cell is cultured in Cardiac Progenitor Culture (CPC) medium, as described hereinbefore In a preferred embodiment, the single LIFR+ and/or FGFR3+ human cardiac ventricular progenitor cell is cultured under conditions such that the cell is biased toward ventricular differentiation. Preferred culture conditions include culture in CPC medium.

In various embodiments, the single LIFR+ and/or FGFR3+ human cardiac ventricular progenitor cell can be expanded to at least $1 \times 10^9$ cells, at least $2 \times 10^9$ cells, at least $3 \times 10^9$ cells, at least $4 \times 10^9$ cells, at least $5 \times 10^9$ cells, at least $6 \times 10^9$ cells, at least $7 \times 10^9$ cells, at least $8 \times 10^9$ cells, at least $9 \times 10^9$ cells or at least $10 \times 10^9$ cells.

Accordingly, the invention also provides a clonal population of at least $1 \times 10^9$ LIFR+ and/or FGFR3+ human cardiac ventricular progenitor cells, which are obtainable or obtained by the methods of the invention for obtaining a clonal population of human cardiac ventricular progenitor cells. In various embodiments, the clonal population of LIFR+ and/or FGFR3+ human cardiac ventricular progenitor cells comprises at least $1 \times 10^9$ cells, at least $2 \times 10^9$ cells, at least $3 \times 10^9$ cells, at least $4 \times 10^9$ cells, at least $5 \times 10^9$ cells, at least $6 \times 10^9$ cells, at least $7 \times 10^9$ cells, at least $8 \times 10^9$ cells, at least $9 \times 10^9$ cells or at least $10 \times 10^9$ cells. Differentiation of the progenitor cells to the ventricular lineage in vitro can be achieved by culture under conditions described herein for biasing toward the ventricular lineage. Furthermore, transplantation of the cardiac ventricular progenitor cells in vivo leads to ventricular differentiation in vivo.

The invention also provides pharmaceutical compositions comprising the clonal population of cardiac ventricular progenitor cells. The pharmaceutical compositions typically are sterile and can comprise buffers, media, excipients and the like suitable for pharmaceutical administration. In one embodiment, the pharmaceutical composition comprising the clonal population is formulated onto a three dimensional (3D) matrix. Compositions formulated onto a 3D matrix are particularly preferred for formation of a heart muscle cell patch that can be transplanted in vivo for heart muscle repair. Furthermore, the compositions can be formulated into two dimensional (2D) sheets of cells, such as a muscular thin film (MTF) as described in Domian, I. J. et al. (2009) *Science* 326:426-429. Such 2D sheets of cell tissue also can be used in the formation of a heart muscle cell patch that can be transplanted in vivo for heart muscle repair.

Generation of Human Ventricular Progenitors (HVPs)

Prior to isolation by the aforementioned methods, and optionally obtaining a clonal population by the aforementioned methods, a non-clonal population of human ventricular progenitors (HVPs) can be obtained by culture of human pluripotent stem cells (hPSCs) under appropriate culture conditions to generate the HVPs. An exemplary set of culture conditions, and suitable starting cells, is described in detail in Example 1 and Example 10, also referred to herein as the Human Ventricular Progenitor Generation (HVPG) protocol. Suitable hPSC starting cells include induced pluripotent stem cells (iPSC) and human embryonic stem cells, such as ES cell lines. For the protocol, Wnt/β-catenin signaling first is activated in the hPSCs, followed by an incubation period, followed by inhibition of Wnt/β-catenin signaling. Wnt/β-catenin signaling activation is achieved by incubation with a Gsk3 inhibitor, preferably CHIR98014 (CAS 556813-39-9; commercially available from, e.g., Selleckchem). Wnt/β-catenin signaling inhibition is achieved by incubation with a Porcn inhibitor, preferably Wnt-059 (CAS 1243243-89-1; commercially available from, e.g., Selleckchem or Tocris). The Gsk3 inhibitor is used to promote cardiac mesodermal differentiation, whereas the Porcn inhibitor is used to enhance ventricular progenitor differentiation from mesoderm cells.

Accordingly, in another aspect, the invention provides a method of generating human ventricular progenitors (HVPs) comprising culturing human pluripotent stems cells (hPSCs) in a medium comprising a Gsk3 inhibitor, preferably CHIR98014, for at least 24 hours, more preferably for 2 days or 3 days, followed by culturing the hPSCs in a medium comprising a Porcn inhibitor, preferably Wnt-059 (and lacking the Gsk3 inhibitor), for at least 48 hours such that HVPs are generated. Experiments showed that after 24-hour treatment with CHIR-98014, more than 99% of hPSCs expressed the mesoderm marker Brachyury, and three days later after treatment with CHIR-98014, more than 95% of differentiated cells expressed Mespl, which marks the cardiac mesoderm. Furthermore, 48-hour treatment with Wnt-059 enhanced ventricular progenitor differentiation from mesoderm cells.

Accordingly, with regard to timing of the use of the Gsk3 and Porcn inhibitors, typically, at day 0 of culture, the hPSCs are cultured with the Gsk3 inhibitor, at day 3 of culture the medium is changed to remove the Gsk3 inhibitor and the cells are then cultured with media containing the Porcn inhibitor through day 5 of culture. HVP generation is optimal between days 5 and 7 (inclusive) in culture and peaks at day 6 of culture. Other non-limiting, exemplary details on culture conditions and timing of the use of the Gsk3 and Porcn inhibitors are described in detail in Examples 1 and 10.

In Vivo Tissue Engineering

In vivo transplantation studies described in Example 6 and 7 in which the human ventricular progenitors (HVPs) were transplanted under the kidney capsule in nude mice document the ability of the HVPs to spontaneously assemble into a large wall of mature, functional, human ventricular muscle on the surface of the kidney capsule. Vascularization occurs via a paracrine pathway by calling the murine vasculature to the ventricular muscle wall, while a matrix is generated via a cell autonomous pathway from the progenitors themselves. In vivo intra-myocardial transplantation studies described in Example 8 in which the HVPs were transplanted into the normal murine heart document that the HVPs spontaneously migrate to the epicardial surface, where they expand, subsequently differentiate, and mature into a wall of human ventricular muscle on the surface of the epicardium. Taken together, these studies show that human ventriculogenesis can occur via a completely cell autonomous pathway in vivo via purified HVPs, thereby allowing their use in organ-on-organ in vivo tissue engineering.

The human ventricular myocardium has a limited capacity for regeneration, most of which is lost after 10 years of age (Bergmann, O. et al. (2015) *Cell* 161:1566-1575). As such, new strategies to generate heart muscle repair, regeneration, and tissue engineering approaches during cardiac injury have been a subject of intense investigation in regenerative biology and medicine (Sahara, M. et al. (2015) *EMBO J.* 34:710-738; Segers, V. F. M. and Lee, R. T. (2008) *Nature* 451:937-942). Given the need to achieve coordinated vascularization and matrix formation during tissue engineering of any solid organ, the assumption has been that the formation of an intact 3-D solid organ in vivo will ultimately require the addition of vascular cells and/or conduits, as well as biomaterials and/or decellularized matrix that will allow alignment and the generation of contractile force (Forbes, S. J. and Rosenthal, N. (2014) *Nature Med.* 20:857-869; Harrison, R. H. et al. (2014) *Tissue Eng. Part B Rev.* 20:1-16). The complexity of adding these various components to achieve the formation of a functional solid organ has confounded attempts to reduce this to clinical practice (Webber, M. J. et al. (2014) *Ann. Biomed. Eng.* 43:641-656). Although hPSCs hold great promise, to date, it has not been possible to build a pure, vascularized, fully functional, and mature 3-D human ventricular muscle organ in vivo on the surface of a heart in any mammalian system (Vunjak-Novakovic, G. et al. (2011) *Annu. Rev. Biomed. Eng.* 13:245-267).

The ability of generate billions of purified HVPs from a renewable source of either human ES or iPS cell lines represent a new approach to the generation of functional ventricular muscle in the setting of advanced heart failure. The progenitors can be delivered by intramyocardial injection and then self-migrate to the epicardial surface where they expand and differentiate, losing progenitor markers. Over the course of several week, the cells exit the cell cycle, and proceed to form adult rod-shaped cells that display several independent markers of mature ventricular myocardium including the formation of T tubules, catecholamine responsiveness, loss of automaticity, adult rod shaped conformation with aligned sarcomenric structures, and the ability to generate force that is comparable to other heart muscle patches derived from hPSCs differentiated cardiomyocytes (Tulloch, N. L. et al. (2011) *Circ. Res.* 109:47-59). The scalability of this cell autonomous pathway has allowed the ectopic generation of human ventricular muscle that has a combined thickness in excess of 1.5 cm in thickness, approaching levels that correspond to the human ventricular free wall (Basavarajaiah, S. et al. (2007) *Br. J. Sports Med.* 41:784-788).

The ability to migrate to the epicardial niche, the site of most of the adult heart progenitors at later stages, is a unique feature of HVPs, and mimics the normal niche of these cells during expansion of the ventricular compact zone during ventriculogenesis. Previous studies have shown that the generation of acute ischemic injury and a breakdown in vascular permeability are a pre-requisite for the grafting of relatively small numbers of ES cell derived cardiomyocytes into injured myocardium (van Laake, L. W. et al. (2007) *Stem Cell Res.* 1:9-24; Laflamme, M. A. et al. (2007) *Nat. Biotechnol.* 25:1015-1024), and even then the survival rate is low (<5%) (Laflamme, M. A. and Murry, C. E. (2011) *Nature* 473:326-335; Laflamme, M. A. et al. (2005) *Am. J. Pathol.* 167:663-671). The ability of intra-myocardial HVPs to form an extensive ventricular patch on the epicardial surface in the absence of acute ischemic injury provides a new therapeutic strategy for dilated cardiomyopathy without the need for additional biomaterials, cells, or transfer of exogenous genes and/or RNAs.

The ability to form a 3-D ventricular muscle wall on the epicardial surface of the in vivo normal heart is a unique feature of the ISL1/FZD4/JAG1 ventricular progenitors as later stage progenitors do not display the ability for the formation of three-dimensional ventricular tissue in either the cardiac or non-cardiac context, emphasizing the importance of generating a committed ventricular lineage as well as purifying the specific ventricular progenitor at a specific stage of ventriculogenesis.

Accordingly, the invention provides methods for generating human ventricular tissue in vivo using the HVPs described herein. In one embodiment, the method comprises transplanting the LIFR+ and/or FGFR3+ progenitors into an organ of a non-human animal and allowing the progenitors to grow in vivo such that human ventricular tissue is generated. Preferably, the non-human animal is immunodeficient such that it cannot mount an immune response against the human progenitor cells. In one embodiment, the non-human animal is a mouse, such as an immunodeficient NOD.Cg-Prkdcscid Il2rgtm1Wjl/SzJ mouse or an immunodeficient SCID-beige mouse (commercially available from Charles River France). In one embodiment, the organ is a kidney (e.g., the cells are transplanted under the kidney capsule). In another embodiment, the organ is a heart. In various embodiments, at least $1\times10^6$ cells, at least $2\times10^6$ cells, at least $3\times10^6$ cells, at least $4\times10^6$ cells, at least $5\times10^6$ cells, at least $1\times10^7$ cells, at least $5\times10^7$ cells, at least $1\times10^8$ cells, at least $1\times10^9$ cells are transplanted.

To obtain HVPs for transplantation, human pluripotent stem cells (hPSCs) can be cultured in vitro under conditions leading to the generation of HVPs, as described herein (referred to herein as the HVPG protocol). Regarding the timing of transplanting HVPs post in-vitro culture, for optimal ventricular tissue generation the cells should be transplanted at a stage that can be defined based on the cellular markers expressed by the HVPs at the time of transplantation, determined at days post the start of culture, which is defined as day 0 of the HVPG protocol. In one embodiment, the cells are transplanted after the peak of cardiac mesoderm formation, which can be defined as peak expression of the mesodermal marker MESP1. Typically, MESP1 expression is between day 2 and day 4 of culture (inclusive) and peaks at day 3. In one embodiment, the cells are transplanted at the time corresponding to peak Islet-1 expression. Typically, Islet 1 is expressed between day 4 to day 8 of culture (inclusive) and peaks at day 6 of culture. In one embodiment, the cells are transplanted before the peak of NKX2.5 expression. Typically, NKX2.5 expression starts at day 6 of culture, peaks at day 10 of culture and is then maintained afterwards. In one embodiment, the cells are transplanted prior to the peak expression of the downstream genes MEF-2 and TBX-1. Typically, these downstream genes are expressed between day 5 and day 15 of culture (inclusive) and peaks at day 8 of culture. In one embodiment, the cells are transplanted prior to the expression of differentiated contractile protein genes. Typically, the expression of contractile protein genes (including TNNT2 and MYH6) starts from day 10 of culture onward. In certain embodiments, the cells are transplanted at a time when two, three or four of the aforementioned marker patterns are present. In another embodiment, the cells are transplanted at a time when all five of the aforementioned marker patterns are present. In one embodiment, the cells are transplanted between day 4 to day 8 (inclusive) of culture. In a more preferred embodiment, the cells are transplanted between day 5 to day 7 (inclusive) of culture. In the most preferred embodiment, the cells are transplanted on day 6 of culture.

The transplanted cells can be allowed to grow in the non-human animal for a suitable period time to allow for the generation of the desired size, amount or thickness of ventricular tissue. In various embodiments, the cells are allowed to grow for one week, two weeks, one month, two months, three months, four months, five months or six months. The method can further comprise harvesting ventricular tissue from the non-human animal after growth of the cells and differentiation into ventricular tissue.

Methods of Enhancing Cardiac Function

The cardiac ventricular progenitor cells of the invention can be used in vivo to enhance cardiac function by transplanting the cells directly into the heart. It has now been shown that the LIFR+ and/or FGFR3+ progenitors have the capacity to differentiate into all three types of cardiac lineage cells (cardiac myocytes, endothelial cells and smooth muscle cells) (see Example 3). Furthermore, when cultured under conditions that bias toward the ventricular lineage, the LIFR+ and/or FGFR3+ progenitors have now been shown to adopt a predominantly ventricular muscle phenotype when transplanted into the natural ventricle environment in vivo, demonstrating that these progenitor cells "recognize" the ventricular environment and respond and differentiate appropriately in vivo. Since damage to the ventricular environment is largely responsible for the impaired cardiac function in cardiac diseases and disorders, the ability to restore ventricular muscle cells using the ventricular progenitor cells of the invention represents a significant advance in the art.

Accordingly, in another aspect, the invention provides a method of enhancing cardiac function in a subject, the method comprising administering a pharmaceutical composition comprising the clonal population of LIFR+ and/or FGFR3+ cardiac ventricular progenitor cells of the invention to the subject. Preferably, the clonal population is administered directly into the heart of the subject. More preferably, the clonal population is administered directly into a ventricular region of the heart of the subject. In one embodiment, the pharmaceutical composition administered to the subject comprises the clonal population formulated onto a three dimensional matrix.

The methods of the invention for enhancing cardiac function in a subject can be used in a variety of clinical situations involving damage to the heart or reduced or impaired cardiac function. Non-limiting examples of such clinical situations include a subject who has suffered a myocardial infarction and a subject who has a congenital heart disorder. Thus, in another aspect, the invention provides a method of treating a cardiovascular condition, disease or disorder in a subject, the method comprising administering a pharmaceutical composition comprising the clonal population of LIFR+ and/or FGFR3+ cardiac ventricular progenitor cells of the invention to the subject. A therapeutically effective amount of cardiac ventricular progenitor cells can be administered for the treatment of a cardiovascular condition, disease or disorder. Examples of preferred cardiovascular conditions, diseases or disorders include coronary artery disease and acute coronary syndrome.

Methods of Use of Cardiac Ventricular Progenitor Cells In Vitro

The cardiac ventricular progenitor cells of the invention can be used in vitro in the study of various aspects of cardiac maturation and differentiation, in particular in identifying the cells signaling pathways and biological mediators involved in the process of cardiac maturation and differentiation.

Furthermore, since the LIFR+ and/or FGFR3+ cardiac ventricular progenitor cells of the invention are committed to the cardiac lineage and, moreover, are biased toward ventricular differentiation, these progenitor cells also are useful for evaluating the cardiac toxicity of test compounds. All potential new drugs and therapeutics must be evaluated for their toxicity to cardiac cells, before they can be deemed safe for use in humans. Thus, the ability to assess cardiac toxicity in an in vitro culture system is very advantageous. Accordingly, in another aspect, the invention provides a method of screening for cardiac toxicity of test compound, the method comprising providing LIFR+ and/or FGFR3+ human cardiac ventricular progenitor cells;

contacting the cells with the test compound; and measuring toxicity of the test compound for the cells, wherein toxicity of the test compound for the cells indicates cardiac toxicity of the test compound.

In a preferred embodiment, the LIFR+ and/or FGFR3+ human cardiac ventricular progenitor cells are provided by isolating the cells according to the methods described herein. In a particularly preferred embodiment, the cells are isolated by separating LIFR+ and/or FGFR3+ cells from a cell culture comprising cardiac progenitor cells using an anti-LIFR and/or anti-FGFR3 antibody. Preferably, the cells are isolated using FACS or MACS as described herein. In yet another embodiment, the LIFR+ and/or FGFR3+ human cardiac ventricular progenitor cells are further cultured and differentiation into MLC2v+ ventricular cells prior to contacting with the test compound.

The toxicity of the test compound for the cells can be measured by one or more of a variety of different methods for assessing cell viability or other physiological functions. Preferably, the effect of the test compound on cell viability is measured using a standard cell viability assay, wherein reduced cell viability in the presence of the test compound is indicative of cardiac toxicity of the test compound. Additionally or alternatively, cell growth can be measured. Additionally or alternatively, other indicators of physiological functions can be measured, such as cell adhesion, cell signaling, surface marker expression, gene expression and the like. Similarly, a negative effect of the test compound on any of these indicators of physiological function is indicative of cardiac toxicity of the test compound.

The invention further provides a method of identifying a compound that modulates human cardiac ventricular progenitor cell differentiation, the method comprising providing LIFR+ and/or FGFR3+ human cardiac ventricular progenitor cells;

culturing the cells in the presence or absence of a test compound;

measuring differentiation of the cells in the presence or absence of the test compound; and selecting a test compound that modulates human cardiac ventricular progenitor cell differentiation, as compared to differentiation in the absence of the test compound, to thereby identify a compound that modulates human cardiac ventricular progenitor cell differentiation.

In one embodiment, the test compound stimulates human cardiac ventricular progenitor cell differentiation. In another embodiment, the test compound inhibits human cardiac ventricular progenitor cell differentiation. Differentiation of the cells can be measured by, for example, measurement of the expression of differentiation markers appearing on the cultured cells over time, as described herein. In a preferred embodiment, the LIFR+ and/or FGFR3+ human cardiac ventricular progenitor cells are provided by isolating the cells according to the methods described herein. In a particularly preferred embodiment, the cells are isolated by separating LIFR+ and/or FGFR3+ cells from a cell culture comprising cardiac progenitor cells using an anti-LIFR and/or anti-FGFR3 antibody. Preferably, the cells are isolated using FACS or MACS as described herein.

The invention further provides a method of identifying a compound that modulates human ventricular cardiomyocyte function, the method comprising providing LIFR+ and/or FGFR3+ human cardiac ventricular progenitor cells;

culturing the cells in the presence or absence of a test compound under conditions that generate human ventricular cardiomyocytes;

measuring function of the human ventricular cardiomyocytes in the presence or absence of the test compound; and selecting a test compound that modulates human ventricular cardiomyocyte function, as compared to function in the absence of the test compound, to thereby identify a compound that modulates human ventricular cardiomyocyte function.

In one embodiment, the test compound stimulates human ventricular cardiomyocyte function. In another embodiment, the test compound inhibits human ventricular cardiomyocyte function. Function of the cells can be measured by measurement of any suitable indicator of ventricular cell function, including but not limited to, for example, formation of T tubules, acquisition of adult-rod shaped ventricular cardiomyocytes, and ability to generate force in response to electrical stimulation. Suitable assays for measuring such indicators of ventricular cell function are known in the art. In a preferred embodiment, the LIFR+ and/or FGFR3+ human cardiac ventricular progenitor cells are provided by isolating the cells according to the methods described herein. In a particularly preferred embodiment, the cells are isolated by separating LIFR+ and/or FGFR3+ cells from a cell culture comprising cardiac progenitor cells using an anti-LIFR and/or anti-FGFR3 antibody. Preferably, the cells are isolated using FACS or MACS as described herein.

In Vivo Animal Models Using Human Ventricular Progenitor Cells

The development of human iPS and ES cell based models of cardiac disease has opened new horizons in cardiovascular drug development and discovery. However, to date, these systems have had the limitations of being based on 2D structures in cultured cell systems. In addition, the fetal and immature properties of the cells limit their utility and fidelity to the adult heart. Human cardiac disease, in particular heart failure, is a complex, multifactorial, multi-organ disease, that is influenced by environmental, hormonal, and other key organs that are known sites for therapeutic targets, such as the kidney. The ability to build a mature functional human ventricular organ either ectopically or on the surface of the intact normal murine heart opens up a new in vivo model system to allow studies that normally could only be assayed on a mature human ventricular muscle chamber, such as ventricular arrhythmias, generation of contractile force, fibrosis, and the potential for regeneration. Accordingly, the option to study human cardiac disease outside of the in vitro tissue culture systems, and directly in the context of heart failure in vivo, is now clearly possible.

Thus, the human ventricular progenitor cells also can be used to create animal models that allow for in vivo assessment of human cardiac tissue function and for in vivo screening of compounds, such as to determine the cardiac toxicity of a test compound in vivo or to identify compounds that modulate human cardiac tissue differentiation or function in vivo. Accordingly, the invention provides methods for testing the effects of test compounds on human ventricular tissue in vivo using the HVPs described herein. In one embodiment, the method comprises:

transplanting LIFR+ and/or FGFR3+ human ventricular progenitors into an organ of a non-human animal;

allowing the progenitors to grow in vivo such that human ventricular tissue is generated;

administering a test compound to the non-human animal; and evaluating the effect of the test compound on the human ventricular tissue in the non-human animal.

In another embodiment, the method comprises:

administering a test compound to a non-human animal, wherein the non-human animal comprises LIFR+ and/or FGFR3+ human ventricular progenitors transplanted into an organ of the non-human animal; and evaluating the effect of the test compound on the LIFR+ and/or FGFR3+ human ventricular progenitors in the non-human animal.

In one embodiment, the cardiac toxicity of the test compound is evaluated, for example by measuring the effect of the test compound on the viability of the human ventricular tissue or the LIFR+ and/or FGFR3+ human ventricular progenitors in the non-human animal (as compared to the viability of the tissue or progenitors in the absence of the test compound). Cell viability can be assessed by standard methods known in the art.

In another embodiment, the ability of a test compound to modulate cardiac differentiation can be evaluated, for example by measuring the effect of the test compound on the differentiation of the human ventricular tissue or LIFR+ and/or FGFR3+ progenitors in the non-human animal (as compared to the differentiation of the tissue or progenitors in the absence of the test compound). Differentiation of the cells can be measured by, for example, measurement of the expression of differentiation markers appearing on the cells over time.

In another embodiment, the ability of a test compound to modulate cardiac function can be evaluated, for example by measuring the effect of the test compound on the function of the human ventricular tissue or LIFR+ and/or FGFR3+ human progenitors in the non-human animal (as compared to the function of the tissue or progenitors in the absence of the test compound). Function of the tissue or progenitors can be measured by measurement of any suitable indicator of ventricular cell function, including but not limited to, for example, formation of T tubules, acquisition of adult-rod shaped ventricular cardiomyocytes, and ability to generate force in response to electrical stimulation. Suitable assays for measuring such indicators of ventricular cell function are known in the art.

Preferably, the non-human animal is immunodeficient such that it cannot mount an immune response against the human progenitor cells. In one embodiment, the non-human animal is a mouse, such as an immunodeficient NOD.Cg-Prkdcscid Il2rgtm1Wjl/SzJ mouse or an immunodeficient SCID-beige mouse (commercially available from Charles River France). In one embodiment, the organ is a kidney (e.g., the cells are transplanted under the kidney capsule). In another embodiment, the organ is a heart. In various embodiments, at least $1 \times 10^6$ cells, at least $2 \times 10^6$ cells, at least $3 \times 10^6$ cells, at least $4 \times 10^6$ cells, at least $5 \times 10^6$ cells, at least $1 \times 10^7$ cells, at least $5 \times 10^7$ cells, at least $1 \times 10^8$ cells, at least $1 \times 10^9$ cells are transplanted.

To create the animal models, HVPs for transplantation can be obtained as described above by culturing of hPSCs in vitro under conditions leading to the generation of HVPs. Regarding the timing of transplanting HVPs post in-vitro culture, for optimal ventricular tissue generation the cells should be transplanted at a stage that can be defined based on the cellular markers expressed by the HVPs at the time of transplantation, determined at days post the start of culture, which is defined as day 0 of the HVPG protocol. In one embodiment, the cells are transplanted after the peak of cardiac mesoderm formation, which can be defined as peak expression of the mesodermal marker MESP1. Typically, MESP1 expression is between day 2 and day 4 of culture (inclusive) and peaks at day 3. In one embodiment, the cells are transplanted at the time corresponding to peak Islet-1 expression. Typically, Islet 1 is expressed between day 4 to day 8 of culture (inclusive) and peaks at day 6 of culture. In one embodiment, the cells are transplanted before the peak of NKX2.5 expression. Typically, NKX2.5 expression starts at day 6 of culture, peaks at day 10 of culture and is then maintained afterwards. In one embodiment, the cells are transplanted prior to the peak expression of the downstream genes MEF-2 and TBX-1. Typically, these downstream genes are expressed between day 5 and day 15 of culture (inclusive) and peaks at day 8 of culture. In one embodiment, the cells are transplanted prior to the expression of differentiated contractile protein genes. Typically, the expression of contractile protein genes (including TNNT2 and MYH6) starts from day 10 of culture onward. In certain embodiments, the cells are transplanted at a time when two, three or four of the aforementioned marker patterns are present. In another embodiment, the cells are transplanted at a time when all five of the aforementioned marker patterns are present. In one embodiment, the cells are transplanted between day 4 to day 8 (inclusive) of culture. In a more preferred embodiment, the cells are transplanted between day 5 to day 7 (inclusive) of culture. In the most preferred embodiment, the cells are transplanted on day 6 of culture.

The transplanted cells can be allowed to grow in the non-human animal for a suitable period time to allow for the generation of the desired size, amount or thickness of ventricular tissue, prior to administration of the test compound(s). In various embodiments, the cells are allowed to grow for one week, two weeks, one month, two months, three months, four months, five months or six months.

The present invention is further illustrated by the following examples, which should not be construed as further limiting. The contents of figures and all references, patents and published patent applications cited throughout this application are expressly incorporated herein by reference.

EXAMPLES

Example 1

Generation of Human Isl1+ Cardiomyogenic Progenitor Cells by Modulation of Wnt Signaling in Human Pluripotent Stem Cells Temporal modulation of canonical Wnt signaling has been shown to be sufficient to generate functional cardiomyocytes at high yield and purity from numerous hPSC lines (Lian, X. et al. (2012) *Proc. Natl. Acad. Sci. USA* 109:E1848-1857; Lian, X. et al. (2013) *Nat. Protoc.* 8:162-

175). In this approach, Wnt/β-catenin signaling first is activated in the hPSCs, followed by an incubation period, followed by inhibition of Wnt/β-catenin signaling. In the originally published protocol, Wnt/β-catenin signaling activation was achieved by incubation with the Gsk3 inhibitor CHIR99021 (GSK-3 α, $IC_{50}$=10 nM; GSK-3, β $IC_{50}$=6.7 nM) and Wnt/β-catenin signaling inhibition was achieved by incubation with the Porcn inhibitor IWP2 ($IC_{50}$=27 nM). Because we used Gsk3 inhibitor and Wnt production inhibitor for cardiac differentiation, this protocol was termed GiWi protocol. To improve the efficiency of the original protocol and reduce the potential side effects of the small molecules used in the original protocol, a second generation protocol was developed that uses another set of small molecules with higher inhibition potency. In this second generation GiWi protocol, Wnt/β-catenin signaling activation was achieved by incubation with the Gsk3 inhibitor CHIR98014 (CAS 556813-39-9; commercially available from, e.g., Selleckchem) (GSK-3 α, $IC_{50}$=0.65 nM; GSK-3, β $IC_{50}$=0.58 nM) and Wnt/β-catenin signaling inhibition was achieved by incubation with the Porcn inhibitor Wnt-059 (CAS 1243243-89-1; commercially available from, e.g., Selleckchem or Tocris) ($IC_{50}$=74 pM). The Gsk3 inhibitor CHIR98014 was used to promote cardiac mesodermal differentiation, whereas the Porcn inhibitor Wnt-059 was used to enhance ventricular progenitor differentiation from mesoderm cells.

For cardiomyocyte differentiation via the use of these small molecules, hPSCs were maintained on Matrigel (BD Biosciences) coated plates (Corning) in E8 medium (described in Chen, G. et al. (2011) *Nature Methods*, 8:424-429; commercially available; STEMCELL Technologies) or mTeSR1 medium (commercially available; STEMCELL Technologies). Suitable hPSCs include induced pluripotent stem cells (iPSCs) such as 19-11-1, 19-9-7 or 6-9-9 cells (Yu, J. et al. (2009) *Science*, 324:797-801) and human embryonic stem cells (hESCs), such as ES03 (WiCell Research Institute) and H9 cells (Thomson, J. A. et al. (1998) *Science*, 282:1145-1147).

hPSCs maintained on a Matrigel-coated surface in mTeSR1 medium were dissociated into single cells with Accutase (Life Technologies) at 37° C. for 5 minutes and then seeded onto a Matrigel-coated cell culture dish at 100,000-200,000 cells/$cm^2$ in mTeSR1 medium supplemented with 5 µM ROCK inhibitor Y-27632 (Selleckchem) (day −2) for 24 hours. Cells were then cultured in mTeSR1, changed daily. At day 0, cells were then treated with 1 µM Gsk3 inhibitor CHIR98014 (Selleckchem) for 24 hours (day 0 to day 1) in RPMI/B27-ins (500 ml RPMI with 10 ml B27 supplement without insulin). The medium was then changed to the corresponding medium containing 2 µM the Porcn inhibitor Wnt-059 (Selleckchem) at day 3, which was then removed during the medium change on day 5. Cells were maintained in RPMI/B27 (stock solution: 500 ml RMPI medium+10 ml B27 supplement) starting from day 7, with the medium changed every three days. This exemplary culturing protocol for generating cardiomyogenic progenitor cells is illustrated schematically in FIG. 1.

Flow cytometry and immunostaining were performed to examine the expression of particular lineage markers. After 24 hour treatment with CHIR-98014, more than 99% of the hPSCs expressed the mesoderm marker Brachyury. Three days after treatment with CHIR-98014, more than 95% of differentiated cells expressed Mespl, which marks the cardiac mesoderm. The culture protocol not only allowed the cells to synchronously differentiate into the cardiac mesodermal lineage, but also reproducibly generated more than 90% of ventricular myocytes after 14 days of differentiation, as determined by cTnT flow cytometry and electrophysiology analysis.

Figure 2:
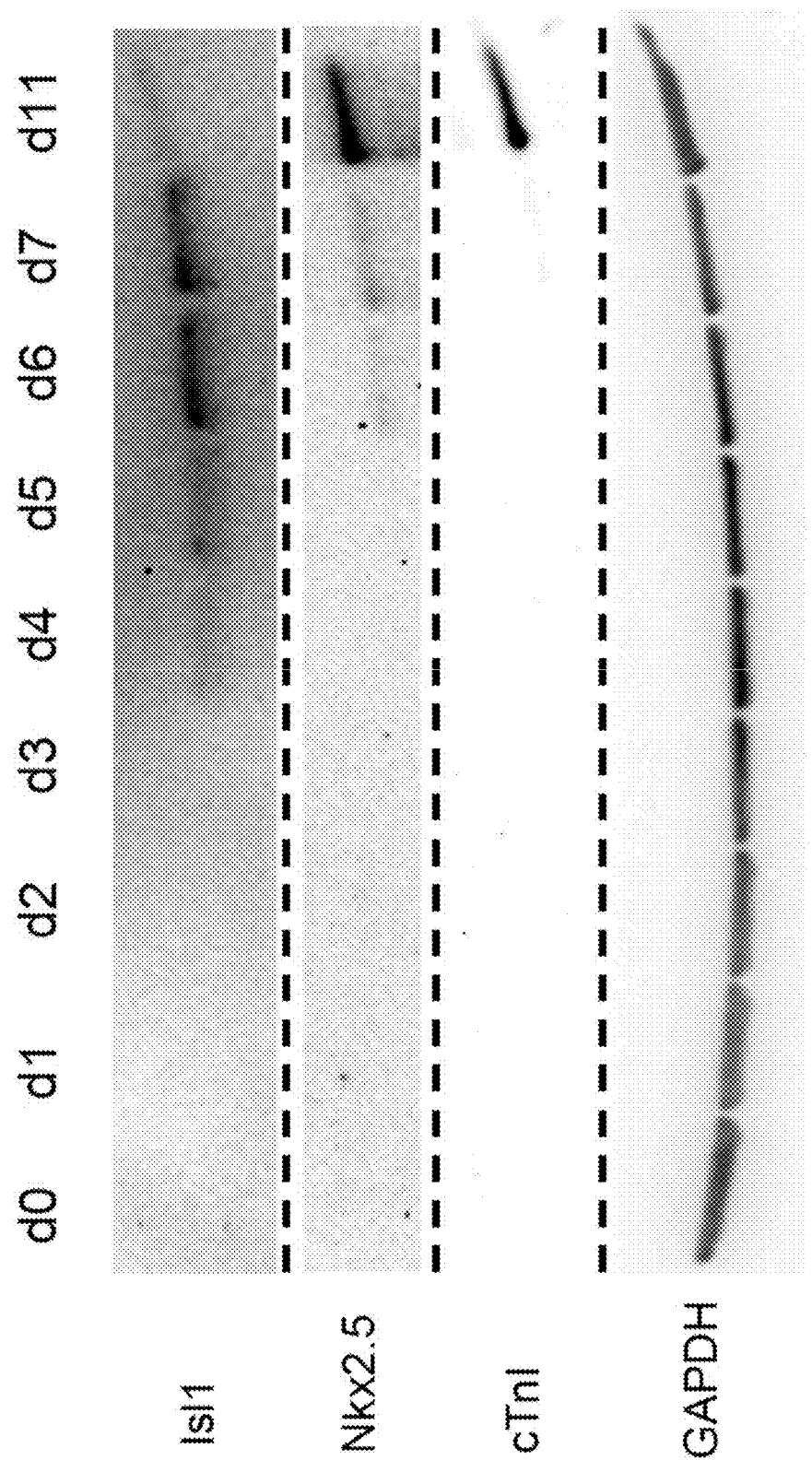
FIG. 2 shows the results of Western blot analysis of protein expression during cardiac differentiation of hPSCs, showing expression of Isl1, Nkx2.5 and cTn1. GAPDH was used as a control.

To further assess cardiac differentiation of the hPSCs over time, Western blot analysis was performed on days 0-7 and d11 to examine the expression of Isl1 and Nkx2.5 (cardiomyogenic progenitor markers) and cTnI (a cardiac myocyte marker). Cells were lysed in M-PER Mammalian Protein Extraction Reagent (Pierce) in the presence of Halt Protease and Phosphatase Inhibitor Cocktail (Pierce). Proteins were separated by 10% Tris-Glycine SDS/PAGE (Invitrogen) under denaturing conditions and transferred to a nitrocellulose membrane. After blocking with 5% dried milk in TBST, the membrane was incubated with primary antibody overnight at 4° C. The membrane was then washed, incubated with an anti-mouse/rabbit peroxidase-conjugated secondary antibody at room temperature for 1 hour, and developed by SuperSignal chemiluminescence (Pierce). The results are shown in FIG. 2. During cardiac differentiation of hPSCs, Isl1 expression started on day 4 and increased to its maximum expression on day 6, whereas NK×2.5 only started to express on day 6 and reached its maximum expression after day 10. Cardiomyocytes (cTnI+ cells) were not induced until day 11 of differentiation.

In addition, immunostaining of the day 6 cells was performed for Isl1 expression. Cells were fixed with 4% formaldehyde for 15 minutes at room temperature and then stained with primary (anti-Isl1) and secondary antibodies in PBS plus 0.4% Triton X-100 and 5% non-fat dry milk (Bio-Rad). Nuclei were stained with Gold Anti-fade Reagent with DAPI (Invitrogen). An epifluorescence microscope (Leica DM IRB) with a QImaging® Retiga 4000R camera was used for imaging analysis. The results showed substantial numbers of Isl1+ cells.

Figure 3:
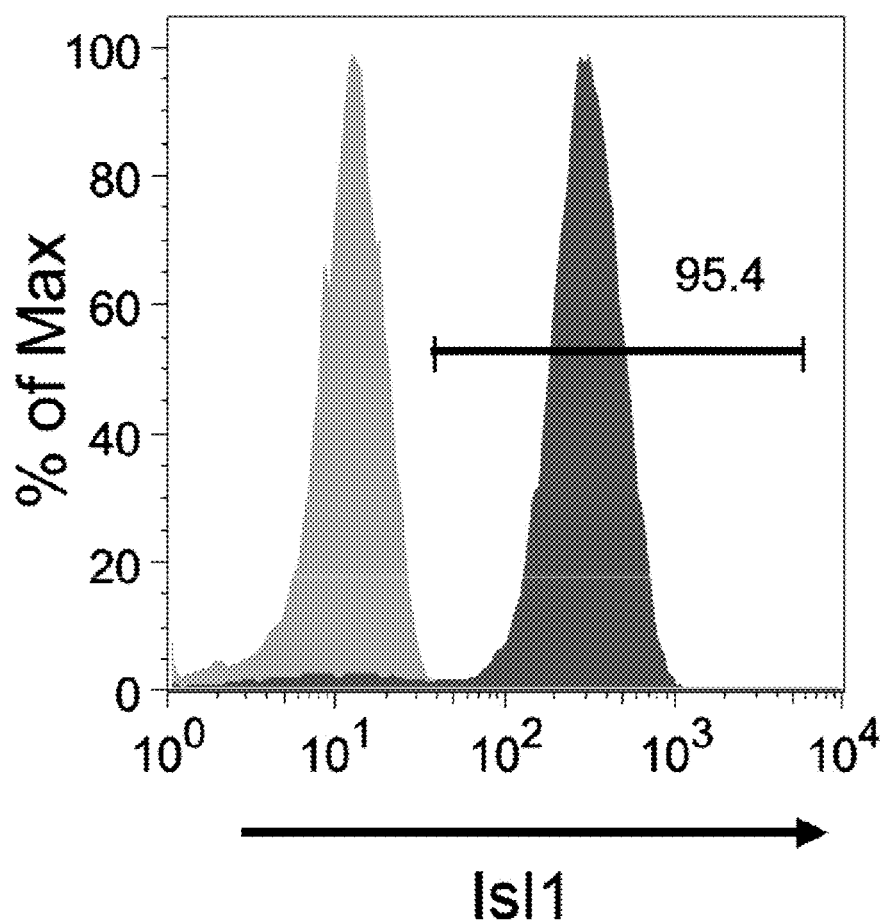
FIG. 3 shows the results of flow cytometry analysis of cardiomyogenic progenitor cells, showing expression of Isl1 on cells at day 6 of differentiation.

Flow cytometry analysis of day 6 cells for Isl1 expression also was performed. Cells were dissociated into single cells with Accutase for 10 minutes and then fixed with 1% paraformaldehyde for 20 minutes at room temperature and stained with primary and secondary antibodies in PBS 0.1% Triton X-100 and 0.5% BSA. Data were collected on a FACSCaliber flow cytometer (Beckton Dickinson) and analyzed using FloJo. The results, shown in FIG. 3, showed that more than 95% of cells expressed Isl1 at this stage.

In summary, this example provides a protocol for human ventricular progenitor generation (HVPG protocol) that allows for the large-scale production of billions of Isl1+ human HPVs efficiently within 6 days.

Example 2

Identification of Jagged 1 as a Cell Surface Marker of Cardiac Progenitor Cells

To profile the transcriptional changes that occur during the cardiac differentiation process at a genome-scale level, RNA sequencing (RNA-seq) was performed at different time points following differentiation to build cardiac development transcriptional landscapes. We performed RNA-seq experiments on day 0 to day 7 samples, as well as day 19 and day 35 samples (two independent biological replicates per time point). Two batches of RNA-seq (100 bp and 50 bp read length) were performed using the illumine Hiseq 2000 platform. In total, 20 samples were examined. Bowtie and Tophat were used to map our reads into a reference human genome (hg19) and we calculate each gene expression (annotation of the genes according to Refseq) using RPKM method (Reads per kilobase transcript per million reads).

Differentiation of hPSCs to cardiomyocytes involves five major cell types: pluripotent stem cells (day 0), mesoderm progenitors (day 1 to day 2), cardiac mesoderm cells (day 3 to day 4), heart field progenitors (day 5, day 6 and day 7), and cardiomyocytes (day 10 after).

Molecular mRNA analysis of cardiac differentiation from hPSCs using the HVPG protocol revealed dynamic changes in gene expression, with down-regulation of the pluripotency markers OCT4, NANOG and SOX2 during differentiation. Induction of the primitive streak-like genes T and MIXL1 occurred within the first 24 hours following CHIR-98014 addition, and was followed by upregulation of the cardiac mesodermal marker MESP1 on day 2 and day 3. Expression of the cardiac muscle markers TNNT2, TNNC1, MYL2, MYL7, MYH6, MYH7 and IRX4 was detected at later stage of differentiation (after day 10).

By this analysis, genes enriched at each differentiation stage, including mesoderm cells, cardiac progenitors and cardiomyocytes, were identified. Mesoderm cells, which are related to day 1 differentiated cells, express brachyury. We identified potential surface markers for mesoderm cells, including: FZD10, CD48, CD1D, CD8B, IL15RA, TNFRSF1B, TNFSF13, ICOSLG, SEMA7A, SLC3A2, SDC1, HLA-A. Through similar analysis, we also identified surface markers for cardiac mesoderm mespl positive cells, including: CXCR4, ANPEP, ITGA5, TNFRSF9, FZD2, CD1D, CD177, ACVRL1, ICAM1, L1CAM, NGFR, ABCG2, FZD7, TNFRSF13C, TNFRSF1B.

Consistent with western blot analysis, ISL1 mRNA was expressed as early as day 4 and peaked on day 5, one day before its protein expression reached its peak. On day 5 of differentiation (the cardiac progenitor stage, isl1 mRNA expression maximum on day 5, isl1 protein expression maximum on day 6), the day 5 enriched genes were compared with an anti-CD antibody array (a panel of 350 known CD antibodies) and a number of potential cell-surface protein markers were identified. We identified many cell-surface proteins expressed at this stage, including: FZD4, JAG1, PDGFRA, LIFR (CD118), TNFSF9, FGFR3.

The cell surface protein Jagged 1 (JAG1) and Frizzled 4 (FZD4) were selected for further analysis. Jagged 1 expression was further studied as described below and in Examples 3 and 4. Frizzled 4 expression was further studied as described in Example 5.

Figure 4:
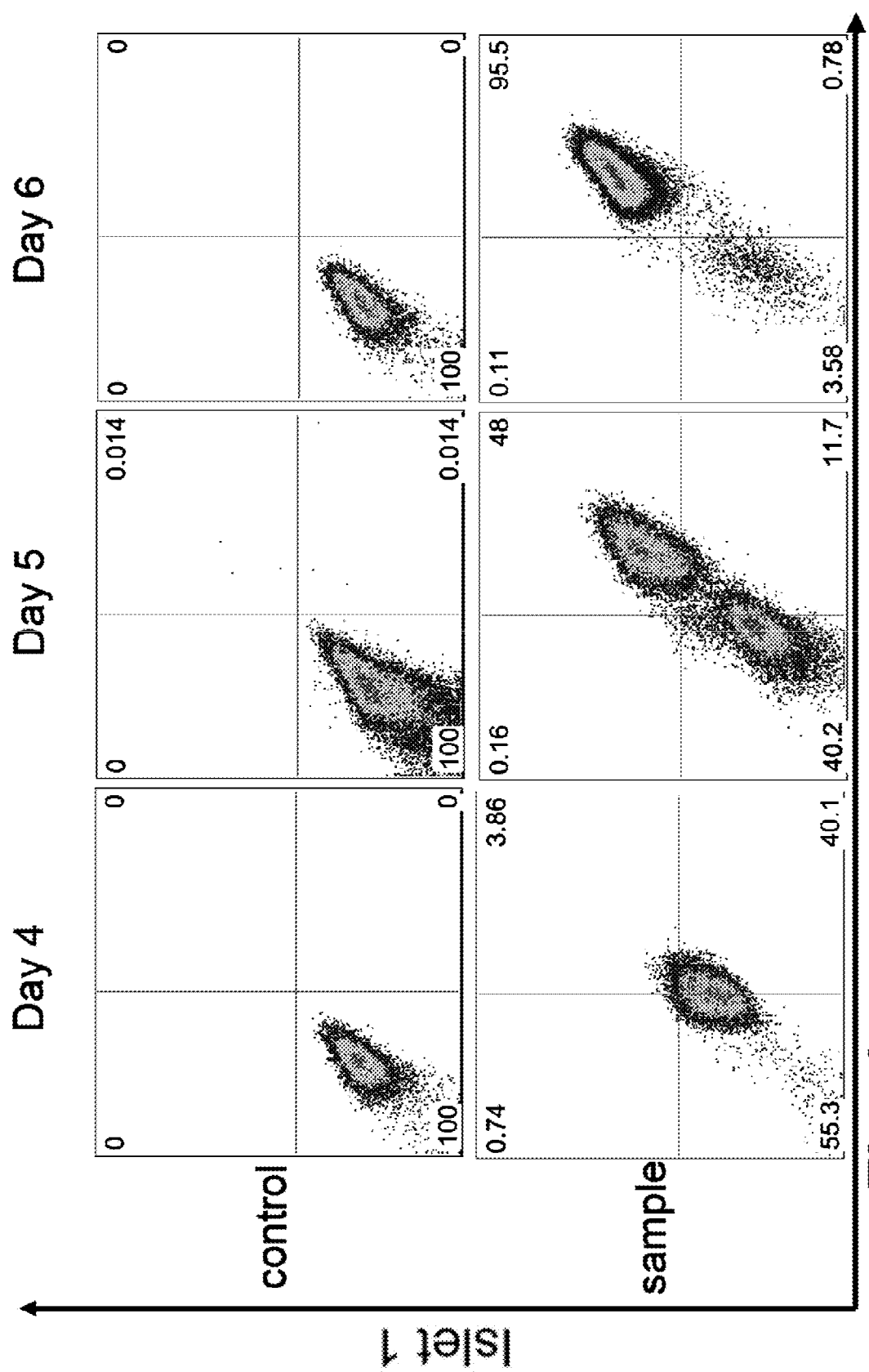
FIG. 4 shows the results of double staining flow cytometry analysis of cardiomyogenic progenitor cells, showing coexpression of Isl1 and Jag1 on cells at day 6 of differentiation.

Firstly, the expression of Isl1 and Jag1 was profiled using the double staining flow cytometry technique. Flow cytometric analysis was carried out essentially as described in Example 1, using anti-Isl1 and anti-Jag1 antibodies for double staining. The results are shown in FIG. 4. Jagged 1 expression was found to trace the expression of Islet 1 and on day 6 of differentiation, all of the Islet 1 positive cells also expressed Jagged 1, and vice versa. Because of the co-expression pattern of these two markers, a Jagged 1 antibody was used to enrich the 94.1% Islet 1+ cells differentiated population to 99.8% purity of Islet1+Jagged1+ cells.

It also was confirmed that Islet 1 is an earlier developmental gene than the Nkx2.5 gene using double immunostaining of ISL1 and NKX2.5 expression in HVPs. The purified HVPs uniformly express the ISL1 gene, but at this stage, only a few of the cells started to express Nkx2.5.

Furthermore, immunostaining with both anti-Isl1 and anti-Jag 1 was performed, essentially as described in Example 1, on week 4 human fetal heart tissue, neonatal heart tissue and 8-year old heart tissue. The results revealed that in the in vivo fetal heart, all of the Islet 1 positive cells also expressed Jagged 1. However, the neonatal heart and 8-year old heart did not express Islet 1 or Jagged 1. In the ventricle of week 4 human fetal heart, cardiac Troponin T (cTnT) staining revealed visible sarcomere structures. In addition, over 50% of ventricular cells in the week 4 fetal heart expressed both Islet1 and Jagged1, which was markedly decreased during subsequent maturation, with the loss of expression of both Islet1 and Jagged1 in the ventricular muscle cells of the human neonatal hearts.

The above-described experiments demonstrate that Jagged 1 is a cell surface marker for Islet 1 positive cardiomyogenic progenitor cells.

Example 3

Clonal Differentiation of Isl1+Jag1+ Cardiac Progenitor Cells

To characterize the clonal differentiation potential of Isl1+Jag1+ cells, cardiomyogenic progenitor cells were generated by the culturing protocol described in Example 1, and one single Isl1+Jag1+ cell was seeded into one well of a Matrigel-coated 48-well plate. Cells were purified with antibody of Jag1 and then one single cell was seeded into one well. The single cells were then cultured for 3 weeks in Cardiac Progenitor Culture (CPC) medium (advanced DMEM/F12 supplemented with 2.5 mM GlutaMAX, 100 µg/ml Vitamin C, 20% Knockout Serum Replacement).

Immunostaining of the 3-week differentiation cell population was then performed with three antibodies: cardiac troponin I (cTn1) for cardiomyocytes, CD144 (VE-cadherin) for endothelial cells and smooth muscle actin (SMA) for smooth muscle cells. The results showed that the single cell-cultured, Isl1+Jag1+ cells gave rise to cTnI positive and SMA positive cells, but not VE-cadherin positive endothelial cells, indicating these generated Islet1+ cells are heart muscle progenitors that have limited differentiation potential to endothelial lineages. Purified Islet1+Jagged1+ cells differentiated with the HVPG protocol from human induced pluripotent stem cells (iPSC 19-9-11 line) also showed similar in vitro differentiation potential and predominantly differentiate to cTnI+SMA+ cells, but not VE-cadherin+ cells. Over the course of several weeks, the cells expressed the ventricular specific marker MLC2v, indicating that the initial ISL1+ subset was already committed to the ventricular cell fate. Because of the limited vascular differentiation potential of Islet1+ cells generated using the HVPG protocol, these generated Islet1+ cells might represent a distinct progenitor population from the previously reported KDR+ population (Yang, L. et al. (2008) *Nature* 453:524-528) or multipotent ISL1+ cells (Bu, L. et al. (2009) *Nature* 460: 113-117; Moretti, A. et al. (2006) *Cell* 127:1151-1165), which can give rise to all three lineages of cardiovascular cells.

These results demonstrated that the Isl1+Jag1+ cardiomyogenic progenitor cells can be successfully cultured in vitro from a single cell to a significantly expanded cell population ($1 \times 10^9$ cells or greater) that contains all three types of cardiac lineage cells, with a predominance of cardiomyocytes. Furthermore, these cells can be cultured in vitro for extended periods of time, for at least 2-3 weeks, and even for months (e.g., six months or more). Since the cardiomyogenic progenitor cells gradually differentiate into cardiomyocytes, which do not proliferate, a culture period of approximately 2-3 weeks is preferred.

Example 4

In Vivo Developmental Potential of Isl1+Jag1+ Cardiac Progenitor Cells'

The ES03 human embryonic stem cell (hESC) line (obtained from WiCell Research Institute) expresses green fluorescent protein (GFP) driven by the cardiac-specific cTnT promoter. ES03 cells were used to generate Isl1+Jag1+ cardiomyogenic progenitor cells using the culturing protocol described in Example 1. The Isl1+Jag1+ cardiomyogenic progenitor cells were transplanted into the hearts of severe combined immunodeficient (SCID) beige mice to document their developmental potential in vivo.

Briefly, Isl1+Jag1+ cells were injected (1,000,000 cells per recipient) directly into the left ventricular wall of NOD/SCID-gamma mice in an open-chest procedure. Hearts were harvested 2-3 weeks post surgery, fixed in 1% PFA and sectioned at 10 μm (n=12). Histological analyses of the hearts of the transplanted mice revealed the presence of GFP+ donor cells, detected by epifluorescence and by staining with an anti-GFP antibody, demonstrating that the Isl1+Jag1+ cardiomyogenic progenitor cells were capable of differentiating into cardiomyocytes when transplanted in vivo.

The Isl1+Jag1+ cardiomyogenic progenitor cells were also transplanted directly into infarcted hearts of SCID beige mice ("injured mice"), as compared to similarly transplanted normal mice. When analyzed two weeks later, injured mice transplanted with the Isl1+Jag1+ cardiomyogenic progenitor cells had a larger graft size than the normal mice similarly transplanted, demonstrating the cardiomyocyte regeneration capacity of the Isl1+Jag1+ cardiomyogenic progenitor cells in vivo.

Example 5

Figure 5:
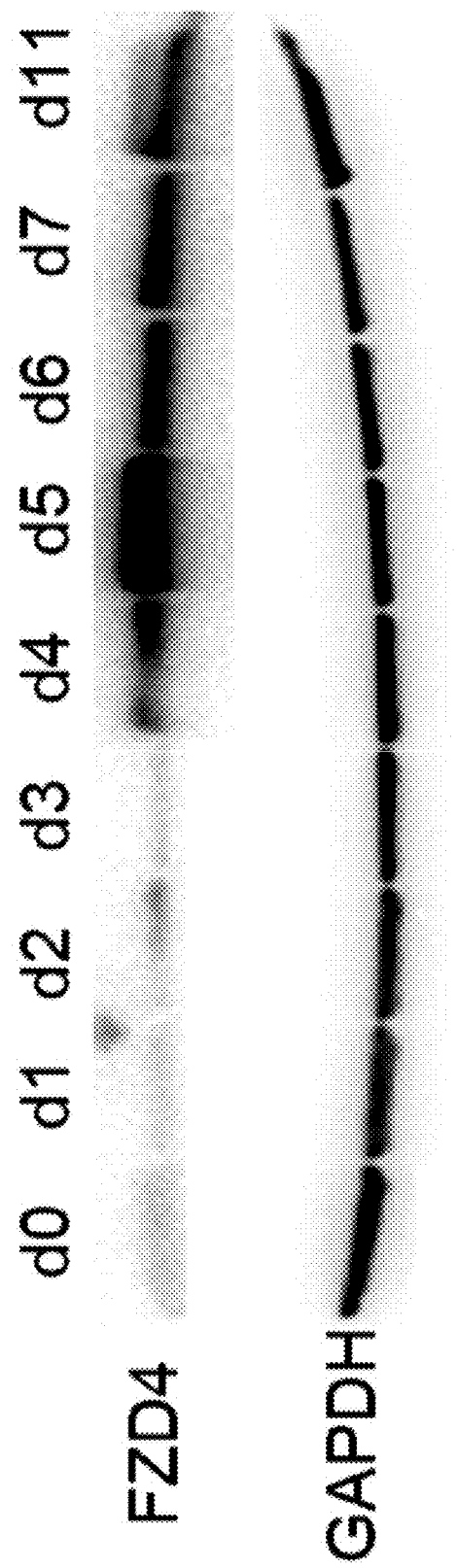
FIG. 5 shows the results of Western blot analysis of protein expression during cardiac differentiation of hPSCs, showing expression of FZD4. GAPDH was used as a control.

Identification of Frizzled 4 as a Cell Surface Marker of Cardiac Progenitor Cells As described in Example 2, Frizzled 4 (FZD4) was identified by RNA-seq analysis as being expressed in cardiac progenitor cells. Thus, to confirm FZD4 as a cell surface marker of cardiac progenitor cells, FZD4 expression was assessed during cardiac differentiation via Western blot analysis. The results, as shown in FIG. 5, demonstrated that FZD4 was not express in pluripotent stem cells and the first 3 days differentiated cells. However, FZD4 started to express on day 4 and maximize its expression on day 5 of expression.

Figure 6:
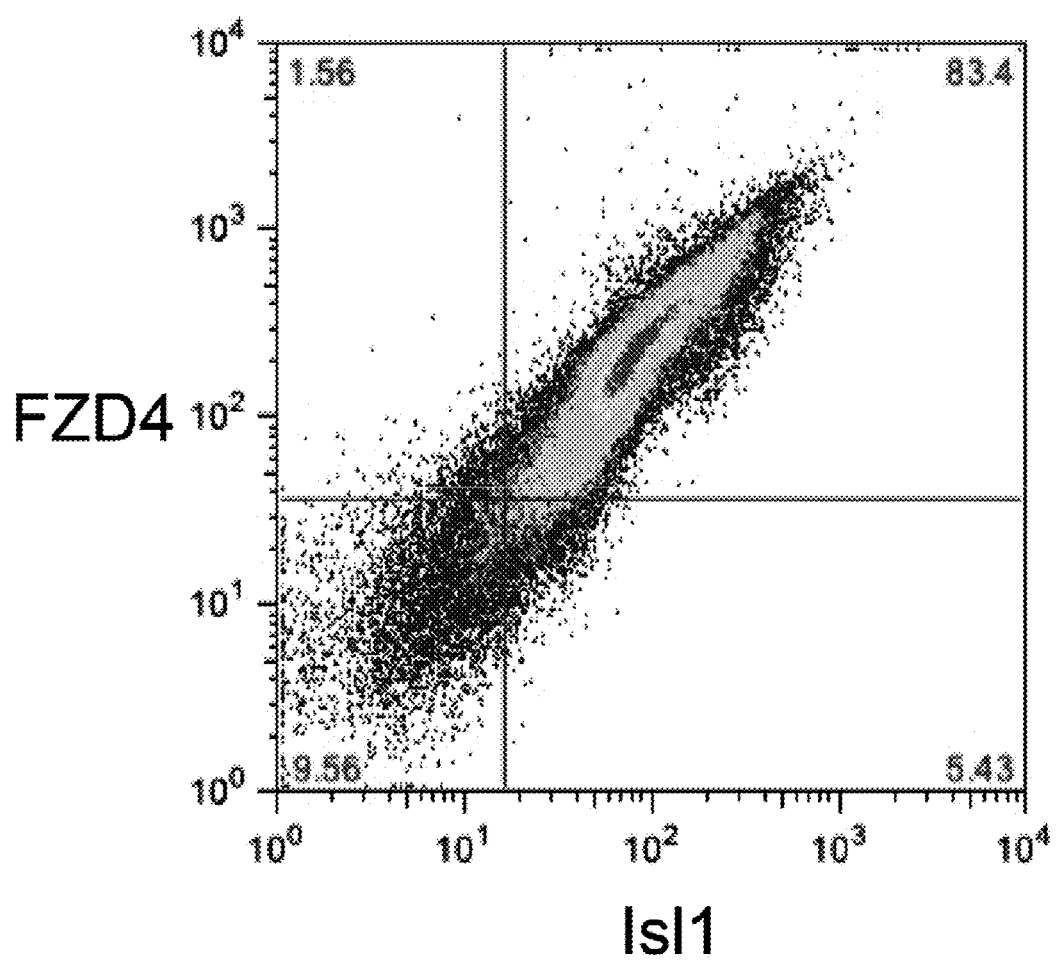
FIG. 6 shows the results of double staining flow cytometry analysis of cardiomyogenic progenitor cells, showing coexpression of Isl1 and FZD4 on cells at day 5 of differentiation.
Figure 7:
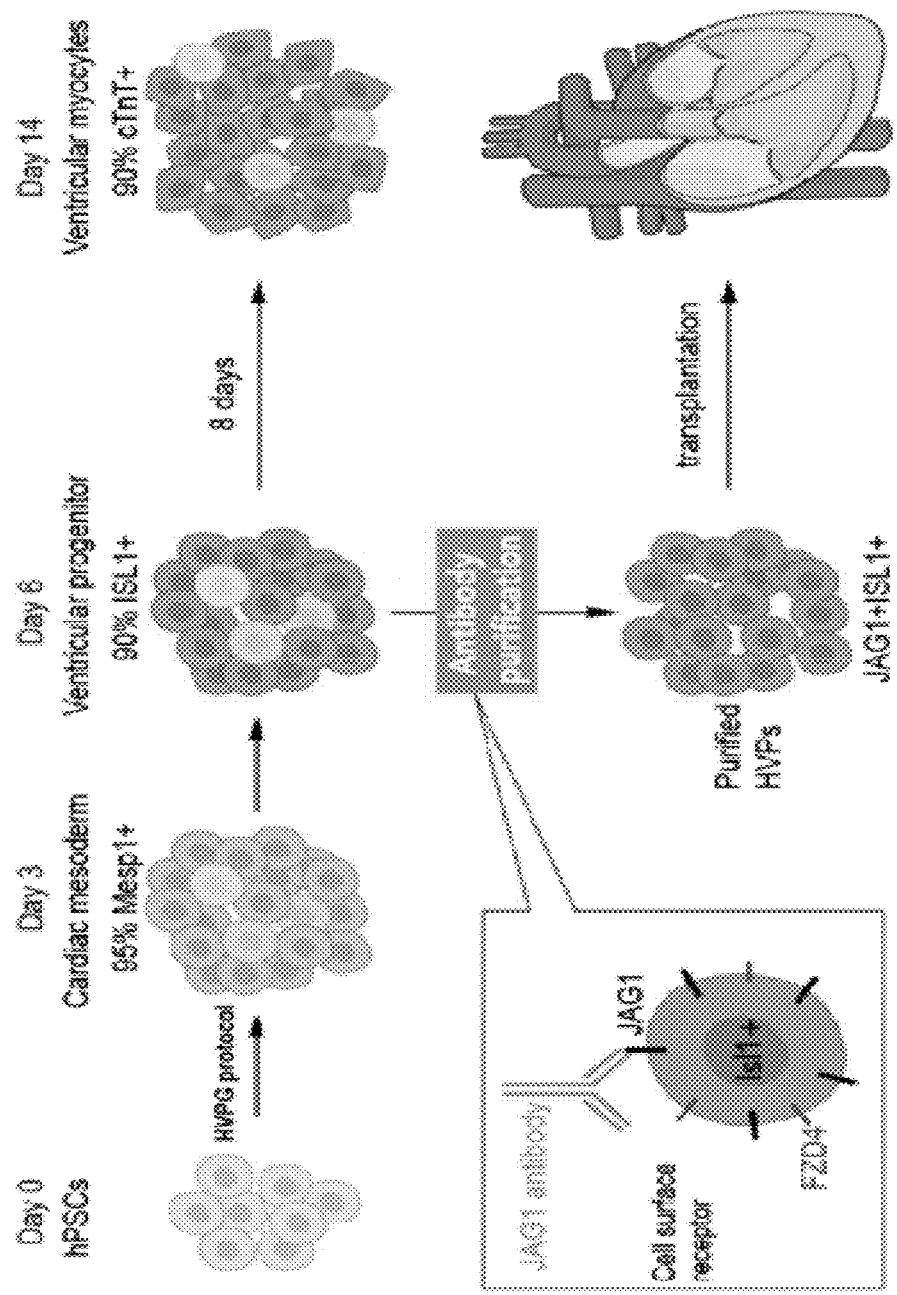
FIG. 7 is a schematic diagram of the generation of human ventricular progenitor (HVP) cells, their ultimate differentiation into ventricular myocytes, their antibody purification and their use in transplantation.

In order to quantify the co-expression pattern of FZD4 and Isl1 at the single cell level, FACS analysis was performed. As shown in FIG. 6, on day 5 of differentiation, more than 83% of cells express both isl1 and FZD4, demonstrating that FZD4 is a cell surface marker for isl1 positive cells during cardiac progenitor differentiation using the GiWi protocol.

In order to confirm that both JAG1 and FZD4 were indeed co-expressed with ISL1 on the human ventricular progenitor cells, triple immunofluorescence analysis of day 6 differentiated cells from hPSCs was performed with antibodies to Islet 1, Jagged 1 and Frizzled 4. The triple staining experiment demonstrated that Isl1+ cells expressed both Jagged 1 and Frizzled 4.

Example 6

Human Ventricular Progenitors (HPVs) Generate a 3-D Ventricular Heart Muscle Organ In Vivo The building of the ventricular heart muscle chamber is one of the most critical and earliest steps during human organogenesis, and requires a series of coordinated steps, including migration, proliferation, vascularization, assembly, and matrix alignment. To test the capacity of HVPs to drive ventriculogenesis in vivo, we transplanted purified HVPs or unpurified HVPs (92.0±1.9% ISL1+) under the kidney capsule of immunocompromised mice. After 2 months post-transplantation, animals transplanted with unpurified HVPs formed tumors, resulting in a tumor formation efficiency of 100% (100%, 4/4), whereas animals transplanted with purified HVPs did not form any tumors (0%, 0/10).

The engrafted kidneys with purified HVPs were further assayed for histological analysis. Hematoxylin and Eosin (H&E) staining revealed an organ that exceeded 0.5 cm in length with more than 1 mm thickness on the surface of the mouse kidney, and that uniformly expressed the ventricular specific marker MLC2v (O'Brien, T. X. et al. (1993) *Proc. Natl. Acad. Sci. USA* 90:5157-5161). The resulting human muscle organ was fully vascularized and red blood cells could be detected in the blood vessels. Analysis of cTnT, MLC2v, and MLC2a immunostaining further revealed that the transplanted HVPs not only differentiated into cardiac muscle cells (cTnT+ cells), but also further mature to become MLC2v+ ventricular myocytes that are negative for MLC2a expression. The resulting ventricular muscle organ is fully vascularized by murine derived vascular cells, consistent with the notion that its vascularization occurred via paracrine cues derived from the HVPs.

The blood vessel structured was revealed by immunostaining analysis of antibodies directed against VE-cadherin and smooth muscle actin expression. In addition, using a human specific monoclonal laminin antibody targeting laminin γ-1 chain, the HVPs secreted their own human laminin as their extracellular matrix (the mouse kidney region is negative for human laminin immunostaining). In addition, we found human fibronectin expression is restricted to areas near the blood vessels using a monoclonal human fibronectin antibody.

To assess the capacity of late stage cardiac cells to drive ventriculogenesis, NKX2.5+ cells (day 10 after differentiation) were transplanted under the kidney capsule of immunocompromised NSG mice. At three weeks post-transplantation, animals transplanted with NKX2.5+ cells did not form any visible human muscle graft, indicating that HVPs lose their ability for in vivo ventriculogenesis following peak Islet-1 expression.

Taken together, these studies indicate that the HVPs can synthesize and release their own cardiac laminin-derived matrix, as well as fibronectin which serves to stabilize the vasculature to the nascent ventricular organ.

Example 7

HVPs Create a Mature, Functioning Ventricular Muscle Organ In Vivo Via a Cell Autonomous Pathway One of the critical limitations for the utility of hPSCs for studies of human cardiac biology and disease is their lack of maturity and persistence of expression of fetal isoforms. To determine if the HVP derived organs could become functional mature ventricular muscle, long term transplantation studies were performed followed by detailed analyses of a panel of well accepted features of adult ventricular myocardium including formation of T tubules (Brette, F. and Orchard, C. (2003) *Circ. Res.* 92:1182-1192; Marks, A. R. (2013) *J. Clin. Invest.* 123:46-52), ability to generate force comparable to other studies of engineered ventricular tissue, loss of automaticity, and acquisition of adult-rod shaped ventricular cardiomyocytes.

After 5 months post-transplantation of purified HVPs, no tumors formed in all of our animals. Animals were sacrificed and the engrafted kidneys were removed for further analysis. The 5-month human graft was a hemisphere structure with the radius of 0.4 cm (diameter of 0.8 cm). The volume for the 5-month human graft was around 0.13 cm$^3$ for one kidney, a volume that suggests feasibility for generating human ventricular muscle that achieves a thickness comparable to the in vivo human adult heart. Rod-shaped mature human ventricular myocytes were observed in the human muscle organ. In addition, muscle trips taken from our mature human muscle organ generated forces (0.36±0.04 mN) in response to electric stimulation and increased their force generation after treatment with a β-adrenergic agonist isoprenaline (0.51±0.02 mN, p<0.05 compared to control). Taken together, these studies indicate that the HVPs are capable of generating a fully functional, mature human ventricular muscle organ in vivo via a cell autonomous pathway, i.e., without the addition of other cells, genes, matrix proteins, or biomaterials.

Example 8

HVPs Migrate Towards an Epicardial Niche and Spontaneously Form a Human Ventricular Muscle Patch on the Surface of a Normal Murine Heart In Vivo The epicardium is a known niche for heart progenitors, driving the growth of the ventricular chamber during compact zone expansion, as well as serving as a home to adult epicardial progenitors that can expand after myocardial injury and that can drive vasculogenesis in response to known vascular cell fate switches, such as VEGF (Giordano, F. J. et al. (2001) *Proc. Natl. Acad. Sci. USA* 98:5780-5785; Masters, M. and Riley, P. R. (2014) *Stem Cell Res.* 13:683-692; Zangi, L. et al. (2013) *Nat. Biotechnol.* 31:898-907). To determine if the HVPs might migrate spontaneously to the epicardial surface of the normal heart, purified green fluorescent protein (GFP)-labeled HVPs were injected intramyocardially into the hearts of immunocompromised mice. After one week or one month post-transplantation, animals were sacrificed and the engrafted hearts were removed for histology. After one week post-transplantation, the majority of GFP+ cells were retained in the myocardium. However, almost all the GFP+ cells migrated to the epicardium after one month post-transplantation. In addition, GFP+ cells were ISL1+ and Ki67+ after one week post-transplantation.

In order to trace the differentiation potential of Islet1+ cells, the purified ISL1+JAG1+ cells generated from a cTnT promoter driven green fluorescent protein (GFP)-expressing hESC line (H9-cTnT-GFP) were transplanted into the hearts of severe combined immunodeficient (SCID) beige mice to document their developmental potential in vivo. One month after transplantation of Isl1+Jag1+ cells directly into the ventricle of the hearts of SCID beige mice, Hematoxylin and eosin staining revealed a human muscle strip graft present in the epicardium of the murine heart. In addition, immunohistological analyses revealed the presence of GFP+ donor cells detected by epifluorescence and by staining with an anti-GFP antibody. More importantly, when analysed with antibodies of MLC2v and MLC2a, the grafted human muscle strip is positive for MLC2v (100% of cells +), and negative for the atrial marker MLC2a, indicating the transplanted ISL1+ cells not only further differentiated to cardiac muscle cells, but also became ventricular muscle cells.

Taken together, these studies indicate that the HVPs can migrate to an epicardial niche, where they expand, and subsequently differentiate in to a homogenous ventricular muscle patch, again without the addition of exogenous cells, genes, matrices, or biomaterials.

Example 9

Additional Experimental Materials and Methods

In this example, additional details on the experimental materials and methods used in Examples 1-8 are provided.
Maintenance of hPSCs
hESCs (ES03, H9) and human iPSCs (19-9-11) were maintained on Matrigel (BD Biosciences) coated plates in mTeSR1 medium (STEMCELL Technologies) according to previous published methods (Lian, X. et al. (2013) *Nat. Proc.* 8:162-175; Lian, X. et al. (2013) *Stem Cells* 31:447-457).
Human Ventricular Progenitor Generation (HVPG) Protocol
hPSCs maintained on a Matrigel-coated surface in mTeSR1 were dissociated into single cells with Accutase at 37° C. for 10 min and then seeded onto a Matrigel-coated cell culture dish at 100,000-200,000 cell/cm$^2$ in mTeSR1 supplemented with 5 μM ROCK inhibitor Y-27632 (day −2) for 24 hours. At day −1, cells were cultured in mTeSR1. At day 0, cells were treated with 1 μM CHIR-98014 (Selleckchem) in RPMI supplemented with B27 minus insulin (RPMI/B27-ins) for 24 hours (day 0 to day 1), which was then removed during the medium change on day 1. At day 3, half of the medium was changed to the RPMI/B27-ins medium containing 2 μM Wnt-059 (Selleckchem), which was then removed during the medium change on day 5. At day 6, cells were dissociated into single cells and purified with anti-JAG1 or anti-FZD4 antibody.
RNA-Seq Library Construction
RNA was isolated (RNeasy Mini kit, Qiagen), quantified (Qubit RNA Assay Kit, Life Technologies) and quality controlled (BioAnalyzer 2100, Agilent). RNA (800 ng) from each sample was used as input for the Illumina TruSeq mRNA Sample Prep Kit v2 (Illumina) and sequencing libraries were created according to the manufacturer's protocol. Briefly, poly-A containing mRNA molecules were purified using poly-T oligo-attached magnetic beads. Following purification, the mRNA was fragmented and copied into first strand complementary DNA using random primers and reverse transcriptase. Second strand cDNA synthesis was then done using DNA polymerase I and RNase H. The cDNA was ligated to adapters and enriched with PCR to create the final cDNA library. The library was pooled and sequenced on a HiSeq 2000 (Illumina) instrument per the manufacturer's instructions.
RNA-Seq Data Processing
The RNA-seq reads were trimmed and mapped to the hg19 reference using Tophat 2. On average, approximately 23 million reads were generated per sample, and 76% of these reads were uniquely mapped. Expression levels for each gene were quantified using the python script rpkmforgenes and annotated using RefSeq. Genes without at least one sample with at least ten reads were removed from the analysis. Principle Component Analysis and heatmaps were constructed using the R and Gene-E respectively.
Transplantation
Aliquots of 2 million purified HVPs were collected into an eppendorf tube. Cells were spun down, and the supernatant was discarded. Each tube of cells was transplanted under the kidney capsule, or intra-myocardially injected into the heart of the immunodeficient mice, NOD.Cg-Prkdcscid Il2rgtm1Wjl/SzJ or SCID-Beige respectively (Charles River France), following a previously described protocol (Shultz, L. D. et al. (2005) *J. Immunol.* 174:6477-6489). Engrafted Kidneys or hearts are harvested at various time intervals for histological and physiological analysis.

Flow Cytometry

Cells were dissociated into single cells with Accutase for 10 min and then fixed with 1% paraformaldehyde for 20 min at room temperature and stained with primary and secondary antibodies in PBS plus 0.1% Triton X-100 and 0.5% BSA. Data were collected on a FACSCaliber flow cytometer (Beckton Dickinson) and analyzed using FlowJo.

Immunostaining

Cells were fixed with 4% paraformaldehyde for 15 min at room temperature and then stained with primary and secondary antibodies in PBS plus 0.4% Triton X-100 and 5% non-fat dry milk (Bio-Rad). Nuclei were stained with Gold Anti-fade Reagent with DAPI (Invitrogen). An epifluorescence microscope and a confocal microscope (ZEISS, LSM 700) were used for imaging analysis.

Western Blot Analysis

Cells were lysed in M-PER Mammalian Protein Extraction Reagent (Pierce) in the presence of Halt Protease and Phosphatase Inhibitor Cocktail (Pierce). Proteins were separated by 10% Tris-Glycine SDS/PAGE (Invitrogen) under denaturing conditions and transferred to a nitrocellulose membrane. After blocking with 5% dried milk in TBST, the membrane was incubated with primary antibody overnight at 4° C. The membrane was then washed, incubated with an anti-mouse/rabbit peroxidase-conjugated secondary antibody at room temperature for 1 hour, and developed by SuperSignal chemiluminescence (Pierce).

Electrophysiology (Patch Clamping)

Beating ventricular myocyte clusters were microdissected and replated onto glass coverslips before recording. Action potential activity was assessed using borosilicate glass pipettes (4-5 M Ohm resistance) filled with intracellular solution consisting of 120 mM K D-gluconate, 25 mM KCl, 4 mM MgATP, 2 mM NaGTP, 4 mM Na2-phospho-creatin, 10 mM EGTA, 1 mM CaCl2, and 10 mM HEPES (pH 7.4 adjusted with HCl at 25° C.). Cultured cardiomyocytes seeded on coverslip dishes were submerged in extracellular solution (Tyrode's solution) containing 140 mM NaCl, 5.4 mM KCl, 1 mM MgCl2, 10 mM glucose, 1.8 mM CaCl2, and 10 mM HEPES (pH 7.4 adjusted with NaOH at 25° C.). Spontaneous action potentials were recorded at 37° C. using patch clamp technique (whole-cell, current clamp configuration) performed using a Multiclamp 700B amplifier (Molecular Devices, CA, USA) software low-pass filtered at 1 kHz, digitized and stored using a Digidata 1322A and Clampex 9.6 software (Molecular Devices, CA, USA).

Statistics

Data are presented as mean±standard error of the mean (SEM). Statistical significance was determined by Student's t-test (two-tail) between two groups. P<0.05 was considered statistically significant.

Example 10

Xeno-Free Human Ventricular Progenitor Differentiation Protocol

In this example, an alternative differentiation protocol for differentiation of human ventricular progenitors is provided, which utilizes a defined, xeno-free culture medium, Essential 8. The Essential 8 medium was developed for growth and expansion of human pluripotent stem cells (hPSCs) and is described further in Chen, G. et al. (2011) *Nat. Methods* 8:424-429 (referred to therein as "E8" medium).

hPSCs maintained on a Vitronectin (or Laminin 521)-coated surface in Essential 8 medium were dissociated into single cells with Versene solution at 37° C. for 10 min and then seeded onto a Vitronectin (or Laminin 521)-coated cell culture dish at 100,000-200,000 cell/cm$^2$ in Essential 8 medium supplemented with 5 µM ROCK inhibitor Y-27632 (day −2) for 24 hours. At day −1, cells were cultured in Essential 8 medium. At day 0, cells were treated with 0.5 µM CHIR-98014 in RPMI for 24 hours (day 0 to day 1), which was then removed during the medium change on day 1. At day 3, half of the medium was changed to the RPMI medium containing 0.5 µM Wnt-059, which was then removed during the medium change on day 5. At day 6, cells (human ventricular progenitors) were dissociated into single cells and purified with anti-JAG1 or anti-FZD4 antibody. Alternatively cells are purified with anti-LIFR or anti-FGFR3 antibody.

Example 11

Identification of Leukemia Inhibitor Factor Receptor (LIFR) and Fibroblast Growth Factor Receptor 3 (FGFR3) as Cell Surface Markers of Cardiac Progenitor Cells In this example, expression of additional cell surface markers for the cardiac progenitor cells described in Examples 1-8 (i.e., human ventricular progenitor cells) was confirmed by flow cytometry analysis. Human ventricular progenitor (HVP) cells were generated as described in Example 1 or 10 and day 6 cells were analyzed by standard flow cytometry.

FIG. 9 shows the results of a double staining flow cytometry experiment using anti-Islet 1 and anti-Leukemia Inhibitory Factor Receptor (LIFR) antibodies. The results demonstrate that the HVP cells co-express Islet 1 and LIFR, thereby confirming that LIFR is a cell surface marker for the HVP cells.

FIGS. 10A-B show the results of flow cytometry experiments comparing the expression of LIFR and Fibroblast Growth Factor Receptor 3 (FGFR3) on day 6 HVP cells to undifferentiated embryonic stem (ES) cells. The results demonstrate that LIFR and FGFR3 are both highly enriched for expression on the HVP cells, thereby confirming that LIFR and FGFR3 are both cell surface markers for the HVP cells.

EQUIVALENTS

Those skilled in the art will recognize, or be able to ascertain using no more than routine experimentation, many equivalents of the specific embodiments of the invention described herein. Such equivalents are intended to be encompassed by the following claims.

The invention claimed is:

1. A method for isolating human cardiac ventricular progenitor cells, the method comprising:
   1) providing a culture of human embryonic stem (ES) cells or induced pluripotent stem cells (iPSCs);
   2) at day 0, activating Wnt/β-catenin signaling in said culture from step 1;

3) at day 3-5, inhibiting Wnt/β-catenin signaling in said culture from step 2 to generate human cardiac progenitor cells (CPCs);
4) at day 5-7, contacting said human CPCs from step 3 with one or more agents reactive with Leukemia Inhibitory Factor Receptor (LIFR) and/or Fibroblast Growth Factor Receptor 3 (FGFR3);
5) separating LIFR+ cells and/or FGFR3+ cells from negative cells; and
6) isolating the LIFR+ cells and/or FGFR3+ cells as LIFR+ and/or FGFR3+ human cardiac ventricular progenitor cells.

2. The method of claim 1, wherein at step 4) the human CPCs are further contacted with an agent reactive with Islet 1; at step 5) LIFR+ and/or FGFR3+/Islet 1+ cells are separated from negative cells; and at step 6) LIFR+ and/or FGFR3+/Islet 1+ cells are isolated as LIFR+ and/or FGFR3+/Islet 1+ human cardiac ventricular progenitor cells.

3. The method of claim 2, wherein at step 4) the human CPCs are simultaneously contacted with one or more agents reactive with LIFR and/or FGFR3 and the agent reactive with Islet 1.

4. The method of claim 2, wherein at step 4) the human CPCs are contacted with the agent reactive with Islet 1 before contacting with the one or more agents reactive with LIFR and/or FGFR3.

5. The method of claim 2, wherein at step 4) the human CPCs are contacted with the one or more agents reactive with LIFR and/or FGFR3 before contacting with the agent reactive with Islet 1.

6. The method of claim 1, wherein at step 4) the human CPCs are contacted with an anti-LIFR antibody.

7. The method of claim 1, wherein at step 4) the human CPCs are contacted with a soluble LIFR ligand fusion protein.

8. The method of claim 7, wherein the LIFR ligand is LIF.

9. The method of claim 1, wherein the LIFR+ cells and/or FGFR3+ cells are separated from negative cells by fluorescence activated cell sorting or magnetic activated cell sorting.

10. The method of claim 1, wherein the human cardiac ventricular progenitor cells are further cultured and differentiated such that they are Myosin Light Chain 2v (MLC2v) positive.

11. The method of claim 1, wherein at step 4) the human CPCs are contacted with an anti-FGFR3 antibody.

12. The method of claim 1, wherein at step 4) the human CPCs are contacted with a soluble FGFR3 ligand fusion protein.

* * * * *